(12) United States Patent
Rivier et al.

(10) Patent No.: US 7,498,300 B2
(45) Date of Patent: Mar. 3, 2009

(54) CRFR1 SELECTIVE LIGANDS

(75) Inventors: Jean E. F. Rivier, La Jolla, CA (US); Wyle W. Vale, Jr., La Jolla, CA (US); Marilyn H. Perrin, La Jolla, CA (US); Jozsef Gulyas, Julian, CA (US)

(73) Assignee: The Salk Institute for Biological Studies, San Diego, CA (US)

( * ) Notice: Subject to any disclaimer, the term of this patent is extended or adjusted under 35 U.S.C. 154(b) by 685 days.

(21) Appl. No.: 10/763,935

(22) Filed: Jan. 22, 2004

(65) Prior Publication Data

US 2004/0204564 A1 Oct. 14, 2004

Related U.S. Application Data

(63) Continuation of application No. PCT/US02/24238, filed on Jul. 30, 2002.

(60) Provisional application No. 60/309,504, filed on Aug. 1, 2001.

(51) Int. Cl.
*A61K 38/00* (2006.01)
(52) U.S. Cl. .......................................................... 514/9
(58) Field of Classification Search .................. None
See application file for complete search history.

(56) References Cited

U.S. PATENT DOCUMENTS

| | | | |
|---|---|---|---|
| 4,489,163 A | 12/1984 | Rivier et al. | 436/86 |
| 4,605,642 A | 8/1986 | Rivier et al. | 514/12 |
| 5,109,111 A | 4/1992 | Rivier et al. | 530/306 |
| 5,493,006 A | 2/1996 | De Miranda et al. | 530/306 |
| 5,510,458 A | 4/1996 | Kornreich et al. | 530/306 |
| 5,777,073 A | 7/1998 | Rivier | 530/306 |
| 5,824,771 A | 10/1998 | Rivier | 530/306 |
| 5,874,227 A | 2/1999 | Rivier | 435/7.1 |
| 6,214,797 B1 | 4/2001 | Vale, Jr. et al. | 514/12 |
| 6,326,463 B1 | 12/2001 | Rivier | |

FOREIGN PATENT DOCUMENTS

WO   WO 98/54222   12/1998

OTHER PUBLICATIONS

Miranda et al, Constrained Corticotropin-Releasing Factor Antagonist with i-(i+3) Glu-Lys Bridges, J. Med. Chem., 1997, vol. 40, 3651-3658 -Applicant's own work. Reference not included with office action.*

Lawrence, A.J. et al., "The highly selective $CRF_2$ receptor antagonist K41498 binds to presynaptic $CRF_2$ receptors in rat brain", *British Journal of Pharmacology*, 2002, pp. 896-904, vol. 136, No. 6, GB.

Bonk, Ines et al., "Development of a selective photactivatable antagonist for corticotropin-releasing factor receptor, type 2 ($CRF_2$)", *Eur. J. Biochem.*, 2002, pp. 5288-5294, vol. 269.

Rühmann, Andreas et al., "Structural requirements for peptidic antagonists of the corticotropin-releasing factor receptor (CRFR): Development of CRFR2β-selective antisauvagine-30", *Proc. Natl. Acad. Sci.*, Dec. 1998, pp. 15264-15269, vol. 95, USA.

Beyermann et al., "A role for a helical connector between two receptor binding sites of a long-chain peptide hormone", J. Biol. Chem. (2000), vol. 275, No. 8, pp. 5702-5709.

International Search Report issued in PCT/US02/24238 dated Jul. 24, 2007.

* cited by examiner

*Primary Examiner*—Anish Gupta
*Assistant Examiner*—Thomas S Heard
(74) *Attorney, Agent, or Firm*—Fitch, Even, Tabin & Flannery

(57) ABSTRACT

CRF peptide analogs that bind to CRFR1 with an affinity far greater than they bind to CRFR2. These analogs exhibit CRF agonist activity. One exemplary analog that may be made by solid-phase synthesis is (cyclo 31-34)[Ac-$Pro^4$, D-$Phe^{12}$, $Nle^{21,38}$, $Glu^{31}$, $Lys^{34}$]-r/hCRF(4-41).

9 Claims, No Drawings

CRFR1 SELECTIVE LIGANDS

This application is a continuation of PCT US02/24238, filed Jul. 30, 2002, which application claimed priority from U.S. Provisional Application Ser. No. 60/309,504, filed Aug. 1, 2001, the disclosures of which are expressly incorporated hereinafter by reference.

This invention was made with Government support under grant number P01-DK-26741 awarded by the National Institutes of Health. The U.S. Government has certain rights in this invention.

This invention is generally directed to peptides and to the pharmaceutical treatment of mammals using such peptides. More specifically, the invention relates to peptide analogs to the hentetracontapeptide CRF which are selective to one family of CRF receptors, to pharmaceutical compositions containing such CRF analogs, to methods of treatment of mammals using such CRF analogs, and to methods of screening for new drugs using such peptides.

BACKGROUND OF THE INVENTION

Ovine CRF (oCRF) was characterized in 1981 as a 41-residue amidated peptide. oCRF lowers blood pressure in mammals when injected peripherally and stimulates the secretion of ACTH and β-endorphin. Rat CRF (rCRF) was later isolated, purified and characterized; it was found to be a homologous, amidated hentetracontapeptide as described in U.S. Pat. No. 4,489,163. The amino acid sequence of human CRF (hCRF) was determined to be the same as that of rCRF. When given intravenously(iv), hCRF and oCRF have been reported to cause vasodilation of the mesenteric arteries so as to lower blood pressure in mammals and also in stimulating the secretion of ACTH and β-endorphin. However, when administered intracerebroventricularly(icv), there is an elevation of heart rate and mean arterial blood pressure, which are secondary to activation of the sympathetic nervous system.

Although originally isolated and characterized on the basis of its role in this hypothalamopituitary-adrenal (HPA) axis, CRF has been found to be distributed broadly throughout the central nervous system as well as in extraneural tissues, such as the adrenal glands, placenta and testes, where it may also act as a paracrine regulator or a neurotransmitter. Moreover, the likely involvement of CRF in affective disorders, such as anxiety, depression, alcoholism and anorexia nervosa, and in modulating reproduction and immune responses suggests that changes in CRF expression may have important physiological and pathophysiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility.

In addition to its role in mediating activation of the hypothalamic-pituitary-adrenal, CRF has also been shown to modulate autonomic and behavioral changes, some of which occur during the stress response. Many of these behavioral changes have been shown to occur independently of HPA activation in that they are not duplicated by dexamethasone treatment and are insensitive to hypophysectomy. In addition, direct infusion of CRF into the CNS mimics autonomic and behavioral responses to a variety of stressors. Because peripheral administration of CRF fails to affect certain of these changes, it appears that CRF exhibits a direct brain action with respect to such functions, which include appetite suppression, increased arousal and learning ability.

As a result of the extensive anatomical distribution and multiple biological actions of CRF, this regulatory peptide is believed to be involved in the regulation of numerous biological processes. CRF has also been implicated in the regulation of inflammatory responses. Although it has been observed that CRF plays a pro-inflammatory role in certain animal models, CRF appears to suppress inflammation in others by reducing injury-induced increases in vascular permeability.

Recent clinical data have implicated corticotropin-releasing factor ("CRF") in neuropsychiatric disorders and in neurodegenerative diseases, such as Alzeimer's disease. Alzheimer's disease is a neurodegenerative brain disorder which leads to progressive memory loss and dementia. By current estimates, over two million individuals in the United States suffer from this disease. In particular, several lines of evidence have implicated CRF in Alzheimer's disease (AD) (Behan et al., Nature 378(16):284, 1995). First, there are dramatic (greater than 50%) decreases in CRF (Bissette et al., JAMA 254:3067, 1985; DeSouza et al., Brain Research 397: 401, 1986; Whitehouse et al., Neurology 37:905, 1987; DeSouza, Hospital Practice 23:59, 1988; Nemeroff et al., Regul. Peptides 25:123, 1989) and reciprocal increases in CRF receptors (DeSouza et al., 1986; DeSouza, 1988) in cerebrocortical areas that are affected in AD, while neither CRF nor CRF receptors are quantitatively changed in non-affected areas of the cortex (DeSouza et al., 1986). Second, chemical affinity crosslinking studies indicate that the increased CRF receptor population in cerebral cortex in AD have normal biochemical properties (Grigoriadis et al., Neuropharmacology 28:761, 1989). Additionally, observations of decreased concentrations of CRF in the cerebrospinal fluid (Mouradian et al., Neural Peptides 8:393, 1986; May et al., Neurology 37:535, 1987) are significantly correlated with the global neuropsychological impairment ratings, suggesting that greater cognitive impairment is associated with lower CRF concentrations in cerebrospinal fluid (Pomara et al., Biological Psychiatry 6:500, 1989).

Available therapies for the treatment of dementia are severely limited. Tacrine.™., a recently approved drug, leads to only marginal memory improvement in Alzheimer's patients, and has the undesirable side effect of elevating liver enzymes. Alterations in brain CRF content have also been found in Parkinson's disease and progressive supranuclear palsy, neurological disorders that share certain clinical and pathological features with AD. In cases of Parkinson's disease, CRF content is decreased and shows a staining pattern similar to cases of AD (Whitehouse et al., 1987; DeSouza, 1988). In progressive supranuclear palsy, CRF is decreased to approximately 50% of control values in frontal, temporal, and occipital lobes (Whitehouse et al., 1987; DeSouza, 1988).

Some depressive disorders are also associated with decreased levels of CRF. Patients in the depressive state of seasonal depression and in the period of fatigue in chronic fatigue syndrome demonstrate lower levels of CRF in the cerebrospinal fluid (Vanderpool et al., J Clin. Endocrinol. Metab. 73:1224, 1991). Although some depressions have a high improvement rate and many are eventually self-limiting, there are major differences in the rate at which patients recover. A major goal of therapy is to decrease the intensity of symptoms and hasten the rate of recovery for this type of depression, as well as preventing relapse and recurrence. Anti-depressants are typically administered, but severe side effects may result (e.g., suicidality with fluoxetine, convulsions with bupropion). (See Klerman et al. in Clinical Evaluation of Psychotropic Drugs: Principles and Guidelines, R. F. Prien and D. S. Robinson (eds.), Raven Press, Ltd. N.Y., 1994, p. 281.)

Hypoactivation of the stress system as manifested by low CRF levels may play a role in other disorders as well. For examples, some forms of obesity are characterized by a hypoactive hypothalamic-pituitary-adrenal axis (Kopelman et al., Clin. Endocrinol (Oxford) 28:15, 1988; Bernini et al., Horm. Res. 31:133, 1989), some patients with post-traumatic stress syndrome have low cortisol excretion (Mason et al., J. Neu. Men. Dis. 174:145, 1986), and patients undergoing withdrawal from smoking have decreased excretion of adrenaline and noradrenaline, as well as decreased amounts of cortisol in blood (West et al., Psychopharmacology 84:141, 1984; Puddy et al., Clin. Exp. Pharmacol. Physiol. 11:423, 1984). These manifestations all point to a central role for CRF in these disorders because CRF is the major regulator of the hypothalamic-pituitary-adrenal axis. Treatments for these disorders have poor efficacy. For example, the most effective approach to treatment of obesity is a behavior-change program. However, few participants reach goal weight and the relapse rate is high (see Halmi et al. in Clinical Evaluation of Psychotropic Drugs: Principles and Guidelines, R. F. Prien and D. S. Robinson (eds.), Raven Press, Ltd. New York, 1994, p. 547).

In view of the deficiencies in treatments for such disorders and diseases, more effective treatments are needed. The present invention exploits the correlation of reduced levels of CRF with various neuro-physiologically based disorders and diseases to effectively treat such diseases by increasing levels of free CRF, and further provides other related advantages. Because these actions are mediated by CRFR2, CRFR2-selective analogs are preferred over non-selective analogs due to the possible side effects resulting from activation of other CRF receptors.

CRF agonists containing D-isomers of α-amino acids were developed, such as those shown in U.S. Pat. No. 5,109,111. Other agonists of CRF are disclosed in U.S. Pat. No. 5,278, 146. Cyclic CRF agonists exhibiting biopotency were later developed as disclosed in U.S. Pat. Nos. 5,824,771 and 5,844, 074.

CRF-R is used to refer to a family of receptor protein subtypes which participate in the G-protein-coupled response of cells to CRF. CRF-Rs are coupled by heterotrimeric G-proteins to various intracellular enzymes, ion channels, and transporters. The G-proteins associate with the receptor proteins at the intracellular face of the plasma membrane. An agonist binding to a CRF-R catalyzes the exchanges of GTP for GDP on the α-subunit (G-protein "activation"), resulting in its dissociation and stimulation of one (or more) of the various signal-transducing enzymes and channels. G-protein preferentially stimulates particular effectors, and the specificity of signal transduction may be determined, therefore, by the specificity of G-protein/receptor interaction. CRF-R proteins mediate signal transduction through the modulation of adenylate cyclase and perhaps through PI turnover. For example, when CRF binds to and activates the CRF-R, adenylate cyclase causes an elevation in the level of intracellular cAMP. An effective bioassay for evaluating whether a test compound is capable of elevating intracellular cAMP is carried out by culturing cells containing cDNA which expresses CRF receptor proteins in the presence of a potential agonist or antagonist whose ability to modulate signal transduction activity of CRF receptor protein is sought to be determined. Such transformed cells are monitored for either an increase or decrease in the level of intracellular cAMP which provides a determination of the effectiveness of the potential agonist or antagonist. Methods for measuring intracellular levels of cAMP, or measuring cyclase activity, are well known in the art.

The physiological actions of CRF are mediated through activation of at least two high affinity receptors, CRFR1 and CRFR2, which are members of the seven-transmembrane family of receptors [Chen R., et al, P.N.A.S., 90:8967-8971 (1993), Perrin, M., et al., P.N.A.S, 92:2969-2973 (1995), Lovenberg, T., et al., P.N.A.S., 92:836-840 (1995), K. D. Dieterich et al. Exp. Clin. Endocrinol. Diabetes (1997) 105: 65-82 and J. Spiess et al. Trends Endocrinol. Metab. (1998) 9:140-145]. Evidence from transgenic knockouts [A. Contarino et al., Brain Res. (1999) 835:1-9, G. W. Smith et al., Neuron (1998) 20:1093-1102 and P. Timpl et al., Nature Genet. (1998) 19:162-166], antisense oligonucleotide studies [S. C. Heinrichs et al., Regul. Pept. (1997) 71:15-21, G. Liebsch et al., J. Psychiatric Res. (1999) 33:153-163 and T. Skutella et al., Neuroscience (1998) 85: 795-805] and CRFR1 antagonists [K. E. Habib et al., Proc. Natl. Acad. Sci. USA (2000) 97:6079-6084., J. Lundkvist et al., Eur. J. Pharmacol. (1996) 309:195-200., R. S. Mansbach et al., Eur. J. Pharmacol. (1997) 323:21-26 and S. C. Weninger et al., Proc. Natl. Acad. Sci. USA (1999) 96:8283-8288] provide evidence for the involvement of CRFR1 in mediating the anxiogenic effects of CRF.

The CRF2 was identified more recently [T. Kishimoto et al., Proc. Natl. Acad. Sci. USA (1995) 92:1108-1112, W. A. Kostich et al., Mol. Endocrinol. (1998) 12:1077-1085, T. W. Lovenberg et al., Proc. Natl. Acad. Sci. USA (1995) 92:836-840. and M. Perrin et al., Proc. Natl. Acad. Sci. USA (1995) 92:2969-2973] and exists as at least three splice variants. CRFR1 and CRFR2 subtypes are 70% homologous in their amino acid sequences but appear to be pharmacologically [D. P. Behan et al., Mol. Psychiatry (1996) 1:265-277. and K. D. Dieterich et al., Exp. Clin. Endocrinol. Diabetes (1997) 105: 65-82.] and anatomically distinct [D. T. Chalmers et al., J. Neurosci. (1995) 15:6340-6350. and D. H. Rominger et al., J. Pharmacol. Exp. Ther. (1998) 286:459-468].

CRFR1 is distributed throughout the brain and the sensory and motor relay sites, whereas CRFR2 is expressed in regions of the body where there is little or no expression of CRFR1, such as peripheral sites, e.g. the blood vessels, the heart, the GI tract, the lungs and the skin. In addition, while CRFR1 expression is very high in neocortical, cerebellar, and sensory relay structures, CRFR2 expression is generally confined to subcortical structures. Within the pituitary gland, CRFR2 mRNA is detectable at low levels in scattered cells while CRF1 receptor mRNA is readily detectable in anterior and intermediate lobes.

This heterogeneous distribution of CRFR1 and CRFR2 mRNA suggests distinctive functional roles for each receptor in CRF-related systems. CRFR1 may be regarded as the primary neuroendocrine pituitary CRF receptor and important in cortical, cerebellar and sensory roles of CRF.

Both CRFR1 and CRFR2 were found in the pituitary and throughout the neocortex (especially, in prefrontal, cingulate, striate, and insular cortices), amygdala, and hippocampal formation of primates. In primates, both CRFR1 and CRFR2 may be involved in mediating the effects of CRF on cognition, behavior, and pituitary-adrenal function. The presence of CRFR1 (but not CRFR2) within the locus coeruleus, cerebellar cortex, nucleus of the solitary tract, thalamus, and striatum and of CRFR2 (but not CRFR1) in the choroid plexus, certain hypothalamic nuclei, the nucleus prepositus, and the nucleus of the stria terminalis suggests that each receptor subtype also may have distinct functional roles within the primate central nervous system. See, e.g., Sanchez et al., J. Comp. Neurol. 408:365-377.

CRF has been widely implicated as playing a major role in modulating the endocrine, autonomic, behavioral and immune responses to stress. The recent cloning of multiple receptors for CRF as well as the discovery of non-peptide receptor antagonists for CRF receptors have begun a new era of CRF study. Presently, there are five distinct targets for CRF with unique cDNA sequences, pharmacology and localization. These fall into three distinct classes, encoded by three different genes and have been termed the CRFR1 and CRFR2 (belonging to the superfamily of G-protein coupled receptors) and CRF-binding protein.

Expression of these receptors in mammalian cell lines has made possible the identification of non-peptide, high affinity, selective receptor antagonists. While the natural mammalian ligands oCRF and r/hCRF have high affinity for the CRFR1 subtype, they have lower affinity for the CRFR2 family making them ineffective labels for CRF2. [$^{125}$I]Sauvagine has been characterized as a high affinity ligand for both the CRFR1 and the CRFR2 subtypes and has been used in both radioligand binding and receptor autoradiographic studies as a tool to aid in the discovery of selective small molecule receptor antagonists. A number of non-peptide CRFR1 antagonists that can specifically and selectively block the CRFR1 subtype have recently been identified. Compounds such as CP 154,526, NBI 27914 and Antalarmin inhibit CRF-stimulation of cAMP or CRF-stimulated ACTH release from cultured rat anterior pituitary cells. Furthermore, when administered peripherally, these compounds compete for ex vivo [$^{125}$I]sauvagine binding to CRFR1 in brain sections demonstrating their ability to cross the blood-brain-barrier. In in vivo studies, peripheral administration of these compounds attenuate stress-induced elevations in plasma ACTH levels in rats demonstrating that CRFR1 can be blocked in the periphery. Furthermore, peripherally administered CRFR1 antagonists have also been demonstrated to inhibit CRF-induced seizure activity. These data clearly demonstrate that non-peptide CRFR1 antagonists, when administered systemically, can specifically block central CRFR1 and provide tools that can be used to determine the role of CRFR1 in various neuropsychiatric and neurodegenerative disorders. In addition, these molecules will prove useful in the discovery and development of potential orally active therapeutics for these disorders. McCarthy et al., Curr Pharm Des. (1999) 5(5):289-315.

Because the CRFR1 control different functions than the CRFR2, it would be valuable to be able to regulate one family of receptors without significantly affecting the other family. oCRF and rCRF bind substantially similarly to both CRFR1 and CRFR2 families. A. Ruhmann et al. *P.N.A.S.*, 95, 15264-15269 (Dec. 1998) reported that [D-Phe$^{11}$, His$^{12}$]-sauvagine (11-40) was an antagonist that acted selectively with respect to CRFR2 and exhibited competitive antagonism equal to about 30% of that of the then best antagonist for CRFR1 and close to equal antagonism for CRFR2 compared to this previously best reported compound. Thereafter, the search has continued for CRF analogs that will be bioactive as CRFR1-selective agonists and also for analogs that will serve as effective competitive antagonists to modulate the activation of CRFR1 while having less effect upon CRFR2.

SUMMARY OF THE INVENTION

A class of CRF peptides which are ligands of CRFR1 has now been found which are analogs of hCRF/oCRF and preferably have a cyclizing bond between the residues that correspond to residues 31 and 34 of the native CRF molecule, which cyclizing bond is preferably an amide linkage between side chains of the amino acid residues in those positions. The C-terminus of the molecules is the native amide; however the N-terminus is preferably shortened by elimination of the first 3 residues and by acylation of the residue in position 4 at the N-terminus. The comparable linear peptides also show selectivity and high binding strength to the CRFR1; however, they are not believed to be as biopotent. Using techniques well known in this art, selective agonists can be transformed into CRF antagonists that will selectively block the CRFR1 by retaining the disclosed cyclic portion of the core structure.

Pharmaceutical compositions in accordance with the invention include such CRFR1 ligands or nontoxic addition salts thereof that are dispersed in a pharmaceutically acceptable liquid or solid carrier. Such formulation is facilitated because of their high solubility at physiological pH. The administration of such peptides or pharmaceutically acceptable addition salts thereof to mammals, particularly humans, in accordance with the invention may be carried out for the regulation of secretion of ACTH, β-endorphin, β-lipotropin, corticosterone and other products of the pro-opiomelanocortin (POMC) gene and/or for affecting mood, behavioral and gastrointestinal functions and autonomic nervous system activities. For example, these CRF analogs may be administered to increase ACTH levels to treat shock and like conditions. Very generally, administration of a compound of the present invention can be used to treat a wide variety of disorders or illnesses, particularly associated with CRFR1. In particular, the compounds of the present invention may be administered to an animal for the treatment of depression, anxiety disorder, panic disorder, obsessive-compulsive disorder, reactive hypertension, anorexia nervosa, bulimia, irritable bowel syndrome, stress-induced immune suppression and epilepsy.

The peptides also provide the basis for valuable methods for drug screening for even more potent molecules which bind to and/or activate CRF receptors because of their high affinity for CRF receptors, and radioactive analogs can be used as tracers that bind selectively to CRFR1 and are valuable for high throughput screening purposes.

In one particular aspect, the invention provides a 38-residue CRFR1 ligand peptide which binds to CRFR1 with an affinity substantially greater than it binds to CRFR2, which peptide has the following formula, or a nontoxic salt thereof:

$Y_1$-Pro-Pro-$R_6$-Ser-$R_8$-Asp-$R_{10}$-$R_{11}$-D-Phe-$R_{13}$-$R_{14}$-$R_{15}$-Arg-$R_{17}$-$R_{18}$-$R_{19}$-$R_{20}$-$R_{21}$-$R_{23}$-$R_{24}$-$R_{25}$-$R_{26}$-$R_{27}$-$R_{28}$-$R_{29}$-Gln-Glu-$R_{32}$-$R_{33}$-$R_{34}$-Arg-$R_{36}$-$R_{37}$-$R_{38}$-$R_{39}$-$R_{40}$-$R_{41}$-$NH_2$ wherein $Y_1$ is an acyl group having not more than 15 carbon atoms or is radioiodinated tyrosine; $R_6$ is Ile, Met or Nle; $P_8$ is Leu or Ile; $R_{10}$ is Leu or CML; $R_{11}$ is Thr or Ser; $R_{13}$ is His, Tyr or Glu; $R_{14}$ is CML or Leu; $R_{15}$ is CML or Leu; $R_{17}$ is Glu, CML, Asn or Lys; $R_{18}$ is Val, CML, Nle or Met; $R_{19}$ is CML, Leu or Ile; $R_{20}$ is Glu, D-Glu or His; $R_{21}$ is Nle, Leu, CML or Met; $R_{22}$ is Ala, D-Ala, Aib, Thr, Asp or Glu; $R_{23}$ is Arg or Lys; $R_{24}$ is Ala, Gln, Ile, Asn, CML or Aib; $R_{25}$ is Asp or Glu; $R_{26}$ is Gln, Asn or Lys; $R_{27}$ is CML, Glu, Gln or Leu; $R_{28}$ is Ala, Lys, Arg or Aib; $R_{29}$ is Gln, Aib or Glu; $R_{32}$ is Aib or an L- or D-isomer of a natural α-amino acid other than Cys; $R_{33}$ is Aib or an L- or D-isomer of Ser, Asn, Leu, Ala, CML or Ile; $R_{34}$ is Lys or Orn; $R_{36}$ is Lys, Orn, Arg, Har, CML or Leu; $R_{37}$ is CML, Leu, Nle or Tyr; $R_{38}$ is Nle, Met, CML or Leu; $R_{39}$ is Glu, Aib or Asp; $R_{40}$ is Ile, Aib, CML, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; provided that a cyclizing bond may exist between Glu in position 31 and $R_{34}$ and provided further that D-2Nal or D-Leu may be substituted for D-Phe.

In another particular aspect, the invention provides a 38-residue CRFR1 ligand peptide which binds to CRFR1 with an affinity substantially greater than it binds to CRFR$_2$, which peptide has the formula $Y_1$-Pro-Pro-A-D-Xaa-B-Glu-$Xaa_a$-$Xaa_b$-$Xaa_c$-C-$NH_2$ wherein $Y_1$ is an acyl group having not more than 15 carbon atoms or is radioiodinated tyrosine; A is a sequence of 6 amino acid residues that is found between Pro in the 5-position and Phe in the 12-position of r/hCRF or the corresponding sequence of another peptide of the CRF family; D-Xaa is D-Phe, D-2Nal or D-Leu; B is a sequence of 18 amino acid residues that is found between Phe in the 12-position and Ala in position-31 of r/hCRF or the corresponding sequence of another peptide of the CRF family; $Xaa_a$ is any L- or D-natural α-amino acid other than Cys or is Aib; $Xaa_b$ is Aib or an L- or D-isomer of Ser, Asn, Leu, Ala, CML or Ile; $Xaa_c$ is either Lys or Orn, the side chain of which may be linked in an amide cyclizing bond to that of Glu; and C is a sequence of the last 7 amino acid residues of the C-terminal portion of any peptide of the CRF family; provided that Nle or Leu may be substituted for Met in A, B and/or in C.

DETAILED DESCRIPTION OF THE PREFERRED EMBODIMENTS

Because the CRF receptor ligands of the present invention demonstrate activity at the CRFR1 receptor site, they may be used as therapeutic agents for the treatment of a wide range of disorders or illnesses including endocrine, psychiatric, and neurologic disorders or illnesses. More specifically, the CRF receptor ligands of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor ligands of the present invention can be used to treat neuropsychiatric disorders. Neuropsychiatric disorders which may be treatable by the CRF receptor ligands of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF receptor ligands may also be useful in treating stress-induced immune suppression associated with various diseases states, as well as stroke. Other uses of the CRF receptor ligands of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor ligands are disclosed. For the purposes of administration, the compounds of the present invention may be formulated as pharmaceutical compositions. Pharmaceutical compositions comprise a CRF receptor ligand of the present invention and a pharmaceutically acceptable carrier and/or diluent. The CRF receptor ligand should be present in the composition in an amount which is effective to treat a particular disorder, that is, in an amount sufficient to achieve desired CRF activity, and preferably with acceptable toxicity to the patient. Preferably, the pharmaceutical compositions of the present invention may include a CRF receptor ligand in an amount from 0.1 mg to 250 mg per dosage depending upon the route of administration, and more preferably from 1 mg to 60 mg. Appropriate concentrations and dosages can be readily determined by one skilled in the art.

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline, Agl=aminoglycine, Abu=L-2-aminobutyric acid, Dbu=L-2,4-diaminobutyric acid, Dpr=L-2,3-diaminopropionic acid, Hly=L-homolysine and Har=L-homoarginine. In addition the following abbreviations are used: CML=$C^\alpha CH_3$-L-leucine; Aib=$C^\alpha CH_3$-L-alanine or 2-aminoisobutyric acid; Nal=L-α-(1- or 2-naphthyl) alanine, Pal=L-β-(2-,3- or 4-pyridyl)alanine, Cpa=L-(2-, 3-, or 4-chloro) phenylalanine, Aph=L-(2-,3- or 4-amino) phenylalanine, Amp=(2-, 3- or 4-aminomethyl) phenylalanine, and Nic=3-carboxypyridine (or nicotinic acid).

Generally, the CRFR1 ligands include a D-isomer in the 12-position, preferably include a cyclizing linkage between the residues in the 31-position and the 34-position, and have the following amino acid sequence, or are equivalent nontoxic salts thereof:

$Y_1$-Pro-Pro-$R_6$-Ser-$P_8$-Asp-$R_{10}$-$R_{11}$-D-Phe-$R_{13}$-$R_{14}$-$R_{15}$-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-Gln-Glu-$R_{32}$-$R_{33}$-$R_{34}$-Arg-$R_{36}$-$R_{37}$-$R_{38}$-$R_{39}$-$R_{40}R_{41}$-$NH_2$ wherein $Y_1$ is an acyl group having not more than 15 carbon atoms or is radioiodinated tyrosine; $R_6$ is Ile, Met or Nle; $R_8$ is Leu or lie; $R_{10}$ is Leu or CML; $R_{11}$ is Thr or Ser; $R_{13}$ is His, Tyr or Glu; $R_{14}$ is CML or Leu; $R_{15}$ is CML or Leu; $R_{17}$ is Glu, CML, Asn or Lys; $R_{18}$ is Val, CML, Nle or Met; $R_{19}$ is CML, Leu or Ile; $R_{20}$ is Glu, D-Glu or His; $R_{21}$ is Nle, Leu, CML or Met; $R_{22}$ is Ala, D-Ala, Aib, Thr, Asp or Glu; $R_{23}$ is Arg or Lys; $R_{24}$ is Ala, Gln, Ile, Asn, CML or Aib; $R_{25}$ is Asp or Glu; $R_{26}$ is Gln, Asn or Lys; $R_{27}$ is CML, Glu, Gln or Leu; $R_{28}$ is Ala, Lys, Arg or Aib; $R_{29}$ is Gln, Aib or Glu; $R_{32}$ is Aib or an L- or D-isomer of a natural α-amino acid other than Cys; $R_{33}$ is Aib or an L- or D-isomer of Ser, Asn, Leu, Ala, CML or Ile; $R_{34}$ is Lys or Orn; $R_{36}$ is Lys, Orn, Arg, Har, CML or Leu; $R_{37}$ is CML, Leu, Nle or Tyr; $R_{38}$ is Nle, Met, CML or Leu; $R_{39}$ is Glu, Aib or Asp; $R_{40}$ is Ile, Aib, CML, Thr, Glu, Ala, Val, Leu, Nle, Phe, Nva, Gly or Gln; and $R_4$, is Ala, Aib, Ile, CML, Gly, Val, Leu, Nle, Phe, Nva or Gln; provided that a cyclizing bond may exist between Glu in position 31 and $R_{34}$ and provided further that D-2Nal or D-Leu may be substituted for D-Phe.

A particularly preferred group of CRF agonists has the amino acid sequence (including nontoxic salts thereof):

(cyclo 31-34)$Y_1$-Pro-Pro-$R_6$-Ser-$R_8$-Asp-Leu-$R_{11}$-D-Phe-His-$R_{14}$-Leu-Arg-Glu-$R_{18}$-Leu-$R_{20}$-Nle-$R_{22}$-$R_{23}$-Ala-$R_{25}$-Gln-Leu-Ala-$R_{29}$-Gln-Glu-$R_{32}$-$R_{33}$-$R_{34}$-Arg-$R_{36}$-$R_{37}$-Nle-$R_{39}$-$R_{40}$-$R_{41}$-$NH_2$ wherein $Y_1$ is an acyl group having not more than 7 carbon atoms; $R_{20}$ is Glu or D-Glu; $R_{22}$ is Ala or Thr; $R_{29}$ is Gln or Glu; $R_{32}$ is His, Aib, Ala, Gly, Leu, Gln or Glu; $R_{36}$ is Lys or Leu; $R_{37}$ is Leu or CML; $R_{39}$ is Glu or Asp; $R_{40}$ is Ile, CML or Glu; and $R_{41}$ is Ile, Aib or Ala; with the remaining variables being defined as above.

Specific analogs which are considered to be particularly biopotent from the standpoint of increasing ACTH levels are:
cyclo(31-34)[Ac-$Pro^4$, D-$Phe^{12}$, $Nle^{21,38}$, $Glu^{31}$, $Lys^{34}$]-r/hCRF(4-41);
(cyclo 31-34)[Ac-$Pro^4$, D-$Phe^{12}$, $Nle^{21,38}$, $Glu^{31}$, $Lys^{34}$]-oCRF(4-41);
(cyclo 31-34)[Ac-$Pro^4$, D-$Phe^{12}$, $Nle^{21,38}$, $Glu^{31}$, $Aib^{33}$, $Lys^{34}$]-r/hCRF(4-41);

(cyclo 31-34)[Ac-Pro$^4$, D-Phe$^{12}$, Nle$^{21,38}$, CML$^{27}$, Glu$^{31}$, Lys$^{34}$]-r/hCRF(4-41);

(cyclo 31-34)[Ac-Pro$^4$, D-Phe$^{12}$, Nle$^{21,38}$, CML$^{27,40}$, Glu$^{31}$, Lys$^{34}$]-r/hCRF(4-41); and (cyclo 31-34)[Ac-Pro$^4$, D-Phe$^{12}$, Nle$^{21,38}$, CML$^{27,40}$, Glu$^{31}$, Aib$^{33}$, Lys$^{34}$]-r/hCRF(4-41).

The peptides are synthesized by a suitable method, such as by exclusively solid-phase techniques, by partial solid-phase techniques, by fragment condensation or by classical solution addition.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

The peptides are preferably prepared using solid phase synthesis, such as that described by Burgess, K., Solid-Phase Organic Synthesis (John Wiley & Sons 2000) and/or Merrifield, *J. Am. Chem. Soc.*, 85, p 2149 (1964). Thus, CRF analogs can be prepared in a straightforward manner and then simply tested for biological activity, which facilitates the ready preparation and evaluation of CRFR1 ligands. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al. Starting material for a CRFR1 ligand can be prepared, e.g. by attaching α-amino-protected Ile to an MBHA resin.

After the desired amino acid sequence has been completed, the intermediate peptide is removed from the resin support unless it is desired to form the cyclizing bond while attached to the resin, as described hereinafter. Removal is effected by treatment with a reagent, such as liquid hydrogen fluoride (HF), which not only cleaves the peptide from the resin but also cleaves all remaining side chain protecting groups and the alpha-amino protecting group, if still present, to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The cyclizing step for the CRF peptide analog depends, of course, upon the type of linkage which is desired between the residues in the 31- and 34-positions. To effect an amide cyclizing linkage (lactam bridge), cyclization may be carried out while the partially protected peptide remains attached to the resin as disclosed in U.S. Pat. Nos. 5,064,939 and 5,043,322. Such a procedure effectively creates an amide cyclizing bond between the two desired side chains while other residues, such as Asp, Glu and/or Lys, in the peptide intermediate retain their side-chain protection.

When cyclizing via an amide bond between a side-chain carboxyl group of the 31-position residue and a side-chain amino group of the 34-position residue, or vice-versa which is considered to be an equivalent linkage, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The α-amino protecting group on the N-terminal residue, whether or not it is to be acylated, and all of the other side-chain protecting groups remain in place while the two base-labile groups are removed using piperidine or the like. Following this selective removal, the reaction to accomplish cyclization is carried out by treating with BOP which effects substantially complete generation of the amide bond. Following cyclization, the peptide is completely deprotected and cleaved from the resin using a reagent, such as HF. Optionally, a BOC-protecting group can be first removed from the N-terminus using TFA.

Alternatively, cyclizations of peptides by such amide linkages can also be effected using teachings of U.S. Pat. No. 4,115,554, (Sep. 19, 1978); U.S. Pat. No. 4,133,805 (Jan. 9, 1979); U.S. Pat. No. 4,140,767 (Feb. 20, 1979); U.S. Pat. No. 4,161,521 (Jul. 17, 1979); U.S. Pat. No. 4,191,754 (Mar. 4, 1980); U.S. Pat. No. 4,238,481 (Dec. 9, 1980); U.S. Pat. No. 4,244,947 (Jan. 13, 1981); and U.S. Pat. No. 4,261,885 (Apr. 14, 1981).

Set forth hereinafter in the Examples are certain preferred methods for synthesizing these peptides; however, those of skill in the art will readily recognize techniques for synthesizing the invention peptides, see, e.g., Fmoc Solid Phase Peptide Synthesis: A Practical Approach (Oxford Univ Press, 2000); Marshak & Liu, Therapeutic Peptides and Proteins : Formulation, Delivery, and Targeting (Current Communications in Molecular Biology) (Cold Spring Harbor Laboratory 1989); Cabilly, S., Combinatorial Peptide Library Protocols, 1st edition (Humana Press,1998); Crabb, J. W., Techniques in Protein Chemistry V (Academic Press 1994), Lloyd-Williams et al., Chemical Approaches to the Synthesis of Peptides and Proteins (New Directions in Organic and Biological Chemistry) (CRC Press 1997).

A straightforward assay can be carried out using rat anterior pituitary cells in monolayer culture to determine what CRF-activity a candidate peptide will exhibit; the procedure which is used is that generally set forth in *Endocrinology*, 91, 562 (1972). The assay will show whether a candidate peptide will exhibit some activity as a CRF agonist and stimulate ACTH secretion by activating CRF receptors on such cells; in this manner its intrinsic CRF activity is measured via the use of high doses. A candidate CRFR1 ligand is also easily evaluated in a binding assay using known CRF receptors, such as that described in Perrin, M., et al., *Endocrinology*, 118, 1171-1179 (1986). CRF receptors and the details of binding assays are discussed later in this specification. Very generally, a binding assay may be carried out with human CRF-R1 using a radioligand such as (cyclo 30-33)[I$^{125}$-D-Tyr$^{12}$, Glu$^{30}$, Lys$^{33}$, Nle$^{21,38}$]-r/hCRF(12-41) or its analog having D-His$^{32}$, which have high affinity for the human CRF-R1. For example, the first-named compound has a K$_D$ of 2.0 nanomolar (1.4-2.9) for binding to hCRFR1, which is essentially equal to that of the comparable D-Phe$^{12}$ analog. One such representative binding assay utilizing CRF-R1 receptor is described in Chen, et al., *P.N.A.S.*, 90, 8967-8971 (October 1993). Such assays are advantageously used to screen for potential CRF-like ligands, in peptide or other form, using a labelled cyclic CRF analog, preferably such a labelled cyclic CRF agonist or antagonist with high affinity.

CRF receptors have now cloned and are disclosed in the aforementioned Chen et al. article, in Perrin, M., et al., *P.N.A.S*, 92, 2969-2973 (March 1995), and in Lovenberg, T., et al., *P.N.A.S.*, 92, 836-840 (January 1995). Binding affinity is a term used to refer to the strength of interaction between ligand and receptor. To demonstrate binding affinity for a CRF receptor, the peptides of the invention are easily evaluated using a tracer ligand of known affinity, such as $^{125}$I-radiolabelled oCRF or [D-Tyr$^{12}$, Nle$^{21,38}$]-r/hCRF(12-41), in binding assay experiments which are well known in this art. The results of such assays indicate the affinity at which each ligand binds to a CRF receptor, expressed in terms of $K_i$, an inhibitory binding affinity constant relative to such a known standard. $K_i$ (inhibitory binding affinity constant) is determined using a "standard" or "tracer" radioactive ligand and thus measures the displacement of the tracer from the receptor or binding protein; it is most properly expressed with reference to such tracer. However, so long as these assays are carefully performed under specific conditions with relatively low concentrations of receptor or the like, the calculated $K_i$ will be substantially the same as its dissociation constant $K_D$. Dissociation constant $K_D$ is representative of the concentration of ligand necessary to occupy one-half (50%) of the binding sites of a receptor or the like. It is particularly efficient to test for $K_i$ because only a single tracer need be labelled, e.g. radioiodinated. A given ligand having a high binding affinity for a CRF receptor will require the presence of very little ligand to bind at least 50% of the available binding sites so that the $K_D$ value for that ligand and receptor will be a small number. On the other hand, a given ligand having a low binding affinity for a particular CRF receptor will require the presence of a relatively high level of the ligand to bind 50% of the sites, so that the $K_D$ value for that ligand and receptor will be a large number.

With respect to a particular receptor protein, a CRF analog peptide having a $K_D$ of about 10 nM or less means that a concentration of the ligand (i.e., the CRF analog peptide) of no greater than about 10 nM will be required to occupy at least 50% of the active binding sites of the receptor protein. Such values may be fairly determined from the results obtained using a radioiodinated standard and no more than approximately 0.8 nM of the receptor (approximately 10-20 pmol receptor/mg membrane protein). Preferred peptides provided by this invention have a binding affinity ($K_D$) such that a ligand concentration of about 10 nanomolar or less is required in order to occupy (or bind to) at least 50% of the receptor binding sites, and these are considered to have high affinity. Some of these CRF analog peptides have a binding affinity of about 2 nM or less. Generally, for purposes of this application, a dissociation constant of about 5 nanomolar or lower is considered to be an indication of strong affinity, and a $K_D$ of about 2 nanomolar or less is an indication of very strong affinity. As mentioned above, it is considered to be particularly advantageous that these CRF analog peptides have a substantially higher affinity for CRFR1 so that they are thus selective in their biological effect.

These binding assays employing CRF receptors are straightforward to perform and can be readily carried out with initially identified or synthesized peptides to determine whether such peptides will likely be effective CRFR1 selective ligands. Such binding assays can be carried out in a variety of ways as well known to one of skill in the art. A detailed example of such an assay is set forth in the Perrin, M., et al., *Endocrinology* article. Moreover, the peptides of the present invention which incorporate a radioiodinated tyrosine residue are effective tracers, selective to CRFR1, that may be used in high throughput screenings.

The following Example 1 sets forth a preferred method for synthesizing CRFR1 ligands of interest by the solid-phase technique. These examples are offered by way of illustration and not limitation.

EXAMPLE 1

The synthesis of (cyclo 31-34)[Ac-Pro$^4$, D-Phe$^{12}$, Nle$^{21,38}$, Glu$^{31}$, Lys$^{34}$]-r/hCRF(4-41) having the amino acid sequence: Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Glu-His-Ser-Lys-Arg-Lys-Leu- Nle-Glu-Ile-Ile-NH$_2$ is conducted in a stepwise manner on about 3 grams of a MBHA hydrochloride resin, such as available from Bachem, Inc., having a substitution range of about 0.1 to 0.5 mmoles/gm. resin. The synthesis is performed manually on an MBHA resin that has a substitution of about 0.28 mequiv per gram of resin using a protocol such as that which follows:

| STEP | REAGENTS AND OPERATIONS | MIX TIMES MIN. |
|------|-------------------------|----------------|
| 1 | Methanol(MeOH) wash | 1 |
| 2 | 10% TEA/DCM (v/v)wash | 1 |
| 3 | Methanol(MeOH) wash | 1 |
| 4 | DCM wash (3 times) | 3 |
| 5 | 80 percent TFA plus 5 percent m-cresol in CH$_2$Cl$_2$ | 10 |
| 6 | Methanol(MeOH) wash | 1 |
| 7 | TEA 10% in DCM | 1 |
| 8 | MeOH wash | 1 |
| 9 | TEA 10% in DCM | 1 |
| 10 | DCM wash (3 times) | 3 |
| 11 | BOC-amino acid (4 equiv. in 30 ml. of either DCM or NMP depending upon the solubility of the particular protected amino acid, (1 time) plus DIC (4 equiv) in CH$_2$Cl$_2$ | 20-30 |

After deprotection and neutralization, the peptide chain is built step-by-step on the resin. Generally, one to two mmol. of BOC-protected amino acid in methylene chloride (DCM) is used per gram of resin (e.g. a 2-5 fold excess depending on substitution of the resin), plus one equivalent of 2 molar DIC in methylene chloride, for 20-30 minutes. When BOC-Arg (Tos) is being coupled, a mixture of 50% NMP and methylene chloride is used. Bzl is used as the hydroxyl side-chain protecting group for Ser and Thr. P-nitrophenyl ester(ONp) can be used to activate the carboxyl end of Asn or Gln; for example, BOC-Asn(ONp) can be coupled overnight using one equivalent of HOBt in a 50% mixture of DMF and methylene chloride. The amido group of Asn or Gln is protected by Xan when DIC coupling is used instead of the active ester method. 2-Cl-Z is used as the protecting group for the Lys side chain except for the Lys residue which is to take part in the lactam bridge where Fmoc is used to protect Lys$^{34}$. Tos is used to protect the guanidino group of Arg and the imidazole group of 5 His, and the side-chain carboxyl group of Glu or Asp is protected by OChx except for Glu$^{31}$ which is protected by OFm. At the end of the synthesis, the following composition is obtained:

BOC-Pro-Pro-Ile-Ser(Bzl)-Leu-Asp(OChx)-Leu-Thr(Bzl)-D-Phe-His(Tos)-Leu-Leu-Arg(Tos)-Glu(OChx)-Val-Leu-Glu(OChx)-Nle-Ala-Arg(Tos)-Ala -Glu(OChx)-Gln(Xan)-Leu-Ala-Gln(Xan)-Gln(Xan)-Glu(OFm)-His(Tos)-Ser (Bzl)-Lys(Fmoc)-Arg(Tos)-Lys(2Cl-Z)-Leu-Nle-Glu (OChx)-Ile-Ile-resin support. Xan may have been partially or totally removed by TFA treatment used to deblock the alpha-amino protecting group. The peptide-resin is then treated with TFA to remove the BOC protecting group at the N-terminus. It is then reacted with acetic anhydride to acetylate the proline residue.

Cyclization (lactamization) of residues 31 and 34 is then performed by the method referred to hereinbefore and described more fully as follows. After washes with dichloromethane(DCM) (2×) and 1-methyl-2-pyrrolidinone (NMP) (2×), the OFm/Fmoc groups of Glu$^{31}$ and Lys$^{34}$, respectively, are removed by 20% piperidine in NMP (1×1 min. and 2×10 min.), followed by washing with NMP (2×), 10% ET$_3$N in DCM (v/v) (1×), methanol (MeOH) (2×) and DCM (2×). The peptide-resin is cyclized using a suitable coupling agent, e.g. by reaction at room temperature with twofold excess of HBTU or O-(benzotriazol-1-yl)-1,1,3,3-tetramethyluronium borate (TBTU) in presence of excess diisoproplyethylamine (DIEA) in NMP for 30 minutes. Other suitable reagents are well known and may also be used. After washing, the cyclization may be repeated if desired to assure completion. The completion of the reaction is confirmed by the well known Kaiser ninhydrin test.

The resulting cyclic peptide-resin is cleaved and deprotected by treatment with 1.0 g of p-cresol and 15 ml. hydrogen fluoride (HF) per gram of peptide-resin, first at −20° C. for 20 min. and then at 0° C. for one-half hour. After elimination of the HF under high vacuum, the resin and peptide are washed with dry diethyl ether, and the peptide is then extracted with MeCN:H$_2$O(60:40) plus 0.1% TFA and separated from the resin by filtration.

The peptide is purified by preparative HPLC as described in Marki, et al., *J. Am. Chem. Soc.*, 103, 3178 (1981); Rivier, et al., *J. Chromatography*, 288, 303-328 (1984); and Hoeger, et al., *BioChromatography*, 2, 3, 134-142 (1987). The chromatographic fractions are carefully monitored by HPLC, and only the fractions showing substantial purity are pooled.

To check whether the precise composition is achieved, the r/hCRF analog can be hydrolyzed in sealed evacuated tubes containing constant boiling HCl, 3 μl of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 38-residue peptide structure has been obtained. MS analysis is employed as reported hereinafter.

The peptide is judged to be homogeneous using reversed-phase high performance liquid chromatography (RP-HPLC). It is specifically subjected to RP-HPLC using a Waters HPLC system with a 0.46×25 cm. column packed with 5 μm Cl$_{18}$ silica, 300 Å pore size and TEAP buffers at different pHs. Desalting of the purified peptide is achieved using Buffer A which is an aqueous 0.1% trifluoroacetic acid solution consisting of 1.0 ml. of TFA per 1000 ml. of solution and Buffer B which is 60% acetonitrile. It has a purity of about 98% measured by capillary zone electrophoresis (CZE). Liquid secondary ion mass spectrometry (LSIMS) mass spectra are measured with a JEOL model JMS-HX110 double-focusing mass spectrometer fitted with a Cs$^+$ gun. An accelerating voltage of 10 kV and Cs$^+$ gun voltage between 25 and 30 kV are employed. The measured value of 4471.33 obtained using LSIMS is in agreement with the calculated value of 4470.53.

The synthesis is repeated omitting the cyclization step (i.e. by protecting all Glu residues with OChx and all Lys residues with 2Cl-Z or simply by deblocking the FMOC group with piperidine prior to HF treatment) to produce a comparable linear peptide.

Binding assays with cells expressing human CRFR1 are carried out as described in the Chen et al. *P.N.A.S.*, supra. The affinities of test peptides for CRFR1 and CRFR2 stably expressed in CHO cells were determined by competitive displacement of $^{125}$I-(Nle$^{21}$, Tyr$^{32}$) ovine CRF (for CRFR1) or of [$^{125}$I-Tyr$^o$-]Ucn (for CRFR2) as described. Data from at least 3 experiments were pooled and inhibitory dissociation constant (K$_i$) values (95% confidence limits) were calculated using the LIGAND program of Munson and Rodbard (1980), *Anal. Biochem*, 107:220-239. The cloned hCRFR1 binds the cyclic peptide with high affinity as determined by the competitive displacement of bound radioligand. The K$_i$ was determined to be about 1.5 (0.9-2.6)nM, which may be compared to r/hCRF of about 0.95(0.47-2.0)nM. The linear peptide exhibits a K$_i$ of 2.7 (2.2-3.4)nmol. The difference is dramatic for similar stably transfected CHO cells expressing human CRFR2 where the respective results for the cyclic and linear peptides were 224(140-370)nM and 500(330-770)nM.

The CRF agonists are examined for their effects on the secretion of ACTH and β-endorphin in vitro and also in vivo. In vitro potency to stimulate the secretion of ACTH and β-endorphin by cultured rat pituitary cells is measured using the procedure generally set forth in *Endocrinology*, 91, 562 (1972) and compared either against synthetic oCRF (the laboratory standard) or against r/hCRF (an alternative standard). In vivo testing is carried out using the general procedure set forth in C. Rivier et al., *Science*, 218, 377 (1982). In vitro testing of the cyclic peptide shows a potency substantially greater that of the standard (oCRF), whereas the linear peptide shows a lesser potency but still greater than the standard. The cyclic peptide shows a significant lowering of blood pressure when administered peripherally.

EXAMPLE 2

The peptide (cyclo 31-34)[Ac-Pro$^4$, D-Phe$^{12}$, Nle$^{21,38}$, Glu$^{31}$, Lys$^{34}$]-oCRF(4-41) having the amino acid sequence:

Ac-Pro-Pro-Ile-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Gln-Glu-His-Ser-Lys-Arg-Lys- Leu-Nle-Asp-Ile-Ala-NH$_2$ is synthesized using a procedure generally as set forth in Example 1. A portion of the peptide-resin is removed prior to cyclization, and it is cleaved and deprotected to provide the corresponding linear peptide. The cyclic peptide strongly stimulates the secretion of ACTH and β-END-LI and causes a very significant lowering of blood pressure when administered peripherally. The linear peptide has very significantly lesser bioactivity. However, both peptides bind strongly to CHO cells expressing CRFR1 and poorly to CHO cells expressing CRFR2.

EXAMPLE 3 A

The peptide (cyclo 31-34)[Ac-Pro$^4$, D-Phe$^{12}$, Nle$^{18,21}$, Glu$^{31}$, Lys$^{34}$]-AHC(4-41) having the amino acid sequence:

Ac-Pro-Pro-Ile-Ser-Leu-Asp-Leu-Thr-D-Phe-His-Leu-Leu-Arg-Glu-Nle-Leu-Glu-Nle-Ala-Lys-Ala-Glu-Gln-Glu-Ala-Glu-Gln-Glu-Ala-Leu-Lys-Arg-Leu- Leu-Leu-Glu-Glu-Ala-NH$_2$ is synthesized using a procedure generally as set forth in Example 1. A portion of the peptide-resin is removed prior to cyclization, and it is cleaved and deprotected so as to provide the corresponding linear peptide. The cyclic peptide strongly stimulates the secretion of ACTH and β-END-LI and causes a very significant lowering of blood pressure when administered peripherally. The linear peptide has very significantly lesser bioactivity. Both peptides bind strongly to CRFR1 and only very weakly to CRFR2.

EXAMPLE 3 B

The peptide (cyclo 31-34)[Ac-Pro$^4$, D-Phe$^{12}$, Nle$^{18,21}$, Glu$^{31}$, Lys$^{34}$]-sucker urotensin(4-41) having the amino acid sequence:
Ac-Pro-Pro-Ile-Ser-Ile-Asp-Leu-Thr-D-Phe-His-Leu-Leu-Arg-Asn-Nle-Ile-Glu-Nle-Ala-Arg-Ile-Glu-Asn-Glu-Arg-Glu-Gln-Glu-Gly-Leu-Lys-Arg-Lys- Tyr-Leu-Asp-Glu-Val-NH$_2$ is synthesized using a procedure generally as set forth in Example 1.

The cyclic peptide binds strongly to CRFR1 and only very weakly to CRFR2. It stimulates the secretion of ACTH and β-END-LI and causes a very significant lowering of blood pressure when administered peripherally.

EXAMPLE 3 C

The peptide (cyclo 31-34)[Ac-Pro$^4$, D-Phe$^{12}$, Nle$^{21,38}$, Glu$^{31}$, Lys$^{34}$]-porcine CRF(4-41) having the amino acid sequence:
Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Glu-His-Ser-Lys-Arg-Lys- Leu-Nle-Glu-Asn-Phe-NH$_2$ is synthesized using a procedure generally as set forth in Example 1.

The cyclic peptide binds strongly to CRFR1 and only very weakly to CRFR2. It stimulates the secretion of ACTH and β-END-LI and causes a very significant lowering of blood pressure when administered peripherally.

EXAMPLE 3 D

The peptide (cyclo 31-34)[Ac-Pro$^4$, D-Phe$^{12}$, Nle$^{21,37,38}$, Glu$^{31}$, Lys$^{34}$]-fish CRF(4-41) having the amino acid sequence:
Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Glu-Glu-His-Ser-Lys-Arg-Lys- Nle-Nle-Glu-Ile-Phe-NH$_2$ is synthesized using a procedure generally as set forth in Example 1.

The cyclic peptide binds strongly to CRFR1 and only very weakly to CRFR2. It stimulates the secretion of ACTH and β-END-LI and causes a very significant lowering of blood pressure when administered peripherally.

EXAMPLE 3 E

The peptide (cyclo 31-34)[Ac-Pro$^4$, D-Phe$^{12}$, Nle$^{14,18,24}$, Glu$^{31}$, Lys$^{34}$]-maggy urotensin(4-41) having the amino acid sequence:
Ac-Pro-Pro-Nle-Ser-Ile-Asp-Leu-Thr-D-Phe-His-Nle-Leu-Arg-Asn-Nle-Ile-His-Arg-Ala-Lys-Nle-Glu-Gly-Glu-Arg-Glu-Gln-Glu-Leu-Ile-Lys-Arg-Asn- Leu-Leu-Asp-Glu-Val-NH$_2$ is synthesized using a procedure generally as set forth in Example 1.

The cyclic peptide binds strongly to CRFR1 and only very weakly to CRFR2. It stimulates the secretion of ACTH and β-END-LI and causes a very significant lowering of blood pressure when administered peripherally.

EXAMPLE 3 F

The peptide (cyclo 31-34)[Ac-Pro$^4$, D-Phe$^{12}$, Nle$^{18,21}$, Glu$^{31}$, Lys$^{34}$]-carp urotensin(4-41) having the amino acid sequence:
Ac-Pro-Pro-Ile-Ser-Ile-Asp-Leu-Thr-D-Phe-His-Leu-Leu-Arg-Asn-Nle-Ile-Glu-Nle-Ala-Arg-Asn-Glu-Asn-Gln-Arg-Glu-Gln-Glu-Gly-Leu-Lys-Arg-Lys- Tyr-Leu-Asp-Glu-Val-NH$_2$ is synthesized using a procedure generally as set forth in Example 1.

The cyclic peptide binds strongly to CRFR1 and only very weakly to CRFR2. It stimulates the secretion of ACTH and β-END-LI and causes a very significant lowering of blood pressure when administered peripherally.

EXAMPLE 3 G

The peptide (cyclo 31-34)[Ac-Pro$^4$, D-Phe$^{12}$, Nle$^{14,18,24}$, Glu$^{31}$, Lys$^{34}$]-flounder urotensin(4-41) having the amino acid sequence:
Ac-Pro-Pro-Nle-Ser-Ile-Asp-Leu-Thr-D-Phe-His-Nle-Leu-Arg-Asn-Nle-Ile-His-Arg-Ala-Lys-Nle-Glu-Gly-Glu-Arg-Glu-Gln-Glu-Gln-Ile-Lys-Arg-Asn- Leu-Leu-Asp-Glu-Val-NH$_2$ is synthesized using a procedure generally as set forth in Example 1.

The cyclic peptide binds strongly to CRFR1 and only very weakly to CRFR2. It stimulates the secretion of ACTH and β-END-LI and causes a very significant lowering of blood pressure when administered peripherally.

EXAMPLE 4

A synthesis as in Example 1 is performed, substituting Aib (2-aminoisobutyric acid) for Ser in the 33-position, to produce the following peptide: (cyclo 31-34)[Ac-Pro$^4$, D-Phe$^{12}$, Nle$^{21,38}$, Glu$^{31}$, Aib$^{33}$, Lys$^{34}$]-r/hCRF(4-41), having the amino acid sequence:
(cyclo 31-34)Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln- Gln-Glu-His-Aib-Lys-Arg-Lys-Leu-Nle-Glu-Ile-Ile-NH$_2$. A portion of the peptide-resin is removed prior to cyclization, and it is cleaved and deprotected to provide the corresponding linear peptide. The cyclic peptide strongly stimulates the secretion of ACTH and β-END-LI and causes a very significant lowering of blood pressure when administered peripherally. The linear peptide has very significantly lesser bioactivity. Both peptides bind strongly to CRFR1 and only very weaker to CRFR2.

EXAMPLE 5

A synthesis as in Example 1 is carried out substituting C$^\alpha$MeLeu for Leu$^{15}$ to produce the following peptide: (cyclo 31-34)[Ac-Pro$^4$, D-Phe$^{12}$, CML$^{15}$, Nle$^{21,38}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-CML-Arg-Glu-Val-Leu-Glu-Nle-Ala-Arg-Ala-Glu-Gln-Leu-Ala-Gln-Gln-Glu-His-Ser-Lys-Arg- Lys-Leu-Nle-Glu-Ile-Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 5 A

A synthesis as in Example 1 is performed substituting C$^{60}$ MeLeu for Leu$^{14}$ to produce the following peptide: (cyclo 31-34)[Ac-Pro$^4$, D-Phe$^{12}$, CML$^{14}$, Nle$^{21,38}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-CML-
Leu-Arg-Glu-Val-Leu-Glu-Nle-Ala-Arg-Ala-Glu-Gln-Leu-
Ala-Gln-Gln-Glu-His-Ser-Lys-Arg-Lys- Leu-Nle-Glu-Ile-
Ile-NH$_2$. It

The cyclic peptide binds strongly to CRFR1 and only very weakly to CRFR2. It stimulates the secretion of ACTH and β-END-LI and causes a very significant lowering of blood pressure when administered peripherally.

EXAMPLE 5 B

A synthesis as in Example 1 is carried out substituting C$^{60}$MeLeu for Leu$^{19}$ to produce the following peptide: (cyclo 31-34)[Ac-Pro$^4$, CML$^{19}$, Nle$^{21,38}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-Leu-
Arg-Glu-Val-CML-Glu-Nle-Ala-Arg-Ala-Glu-Gln-Leu-
Ala-Gln-Gln-Glu-His-Ser-Lys-Arg-Lys- Leu-Nle-Glu-Ile-
Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 5 C

A synthesis as in Example 1 is performed substituting C$^\alpha$MeLeu for Leu$^{27}$ to produce the following peptide: (cyclo 31-34)[Ac-Pro$^4$, D-Phe$^{12}$, Nle$^{21,38}$, CML$^{27}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-Leu-
Arg-Glu-Val-Leu-Glu-Nle-Ala-Arg-Ala-Glu-Gln-CML-
Ala-Gln-Gln-Glu-His-Ser-Lys-Arg-Lys- Leu-Nle-Glu-Ile-
Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 5 D

A synthesis as in Example 1 is performed substituting C$^\alpha$MeLeu for Leu$^{37}$ to produce the following peptide: (cyclo 31-34)[Ac-Pro$^4$, D-Phe$^{12}$, Nle$^{21,38}$, Glu$^{31}$, Lys$^{34}$, CML$^{37}$]-r/hCRF(4-41), having the amino acid sequence:

Ac-Pro-Pro-Ile-Ser-Leu-Asp-Leu-Thr-D-Phe-His-Leu-Leu-
Arg-Glu-Val-Leu-Glu-Nle-Ala-Arg-Ala-Glu-Gln-Leu-Ala-
Gln-Gln-Glu-His-Ser-Lys-Arg-Lys- CML-Nle-Glu-Ile-Ile-
NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 5 E

A synthesis as in Example 1 is carried out substituting C$^\alpha$MeLeu for Glu$^{17}$ to produce the following peptide: (cyclo 31-34)[Ac-Pro$^4$, D-Phe$^{12}$, CML$^{17}$, Nle$^{21,38}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-Leu-
Arg-CML-Val-Leu-Glu-Nle-Ala-Arg-Ala-Glu-Gln-Leu-
Ala-Gln-Gln-Glu-His-Ser-Lys-Arg-Lys- Leu-Nle-Glu-Ile-
Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 5 F

The synthesis as in Example 1 is performed substituting C$^\alpha$MeLeu for Leu$^{27}$ and D-His for His$^{32}$ to produce the following peptide: (cyclo 31-34)[Ac-Pro$^4$, D-Phe$^{12}$, Nle$^{21,38}$, CML$^{27}$, Glu$^{31}$, D-His$^{32}$, Lys$^{34}$]-r/hCRF(4-41), having the formula:

Ac-Pro-Pro-Ile-Ser-Leu-Asp-Leu-Thr-D-Phe-His-Leu-Leu-
Arg-Glu-Val-Leu-Glu-Nle-Ala-Arg-Ala-Glu-Gln-CML-
Ala-Gln-Gln-Glu-D-His-Ser-Lys-Arg-Lys- Leu-Nle-Glu-
Ile-Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 6 A

The synthesis of Example 5 C is repeated, but this time also substituting C$^\alpha$MeLeu for Leu$^{14}$, to produce the following peptide: (cyclo 31-34)[Ac-Pro$^4$, D-Phe$^{12}$, CML$^{14,27}$, Nle$^{21,38}$, Glu$^{31}$, Lys$^{34}$]-r/hCRF(4-41), having the formula:

Ac-Pro-Pro-Ile-Ser-Leu-Asp-Leu-Thr-D-Phe-His-CML-
Leu-Arg-Glu-Val-Leu-Glu-Nle-Ala-Arg-Ala-Glu-Gln-
CML-Ala-Gln-Gln-Glu-His-Ser-Lys-Arg-Lys- Leu-Nle-
Glu-Ile-Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 6 B

The synthesis of Example 5 C is repeated again, but this time also substituting C$^\alpha$MeLeu for Val$^{18}$, to produce the following peptide: (cyclo 31-34)[Ac-Pro$^4$, D-Phe$^{12}$, CML$^{18,27}$, Nle$^{21,38}$, Glu$^{31}$, Lys$^{34}$]-r/hCRF(4-41), having the formula:

Ac-Pro-Pro-Ile-Ser-Leu-Asp-Leu-Thr-D-Phe-His-Leu-Leu-
Arg-Glu-CML-Leu-Glu-Nle-Ala-Arg-Ala-Glu-Gln-Leu-
Ala-Gln-Gln-Glu-His-Ser-Lys-Arg-Lys- Leu-Nle-Glu-Ile-
Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 6 C

The synthesis of Example 5 C is repeated once more, also substituting C$^\alpha$MeLeu for Lys$^{36}$, to produce the following peptide: (cyclo 31-34)[Ac-Pro$^4$, D-Phe$^{12}$, Nle$^{21,38}$, CML$^{27,36}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-Leu-
Arg-Glu-Val-Leu-Glu-Nle-Ala-Arg-Ala-Glu-Gln-CML-
Ala-Gln-Gln-Glu-His-Ser-Lys-Arg-CML- Leu-Nle-Glu-Ile-
Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

The above synthesis is generally repeated, substituting D-His for His$^{32}$, to produce the following peptide: (cyclo 31-34)[Ac-Pro$^4$, D-Phe$^{12}$, Nle$^{21,38}$, CML$^{27,36}$, Glu$^{31}$, D-His$^{32}$, Lys$^{34}$]-r/hCRF(4-41), having the amino acid sequence:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-D-His-Ser-Lys-Arg- CML-Leu-Nle-Glu-Ile-Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 6 D

The synthesis of Example 5 C is repeated, substituting C$^α$MeLeu for Leu$^{37}$, to produce the following peptide: (cyclo 31-34)[Ac-Pro$^4$, D-Phe$^{12}$, Nle$^{21,38}$, CML$^{27,37}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Ser-Lys-Arg-Lys- CML-Nle-Glu-Ile-Ile-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 6 E

The synthesis of Example 5 C is repeated again, but this time also substituting C$^α$MeLeu for Ile$^{40}$, to produce the following peptide: (cyclo 31-34)[Ac-Pro$^4$, D-Phe$^{12}$, Nle$^{21,38}$, CML$^{27,40}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Ser-Lys-Arg-Lys- Leu-Nle-Glu-CML-Ile-NH$_2$, and also its linear counterpart.

Purity of about 95% for the peptides is confirmed by HPLC and by capillary zone electrophoresis (CZE) and identity is confirmed by mass spectroscopy (MS). The measured value of 4498.32 obtained using liquid secondary ion mass spectrometry (LSIMS) for the cyclic peptide is in agreement with the calculated value of 4498.56. The linear peptide has a measured value of 4516.45 which corresponds to the calculated value of 4516.57.

Binding assays with cells expressing human CRFR1 are carried out as described with respect to Example 1. Data from at least 3 experiments are pooled and inhibitory dissociation constant (K$_i$) values (95% confidence limits) are calculated using the LIGAND program of Munson and Rodbard (1980), *Anal. Biochem*, 107:220-239. The cloned hCRFR1 binds the cyclic peptide with high affinity as determined by the competitive displacement of bound radioligand. The linear peptide exhibits a slightly higher K$_i$. The difference is significant for similar stably transfected CHO cells expressing human CRFR2 where the respective results for the cyclic and linear peptides show both bind only weakly. The cyclic peptide stimulates the secretion of ACTH and β-END-LI and causes a very significant lowering of blood pressure when administered peripherally.

EXAMPLE 6 F

The synthesis of Example 5 C is repeated again, but this time also substituting C$^{60}$ MeLeu for Ile$^{41}$, to produce the following peptide: (cyclo 31-34)[Ac-Pro$^4$, D-Phe$^{12}$, Nle$^{21,38}$, CML$^{27,41}$, Glu$^{31}$, Lys$^{34}$]-r/hCRF(4-41), having the amino acid sequence:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Ser-Lys-Arg-Lys- Leu-Nle-Glu-Ile-CML-NH$_2$.

The cyclic peptide binds strongly to CRFR1 and only very weakly to CRFR2. It stimulates the secretion of ACTH and β-END-LI and causes a very significant lowering of blood pressure when administered peripherally.

EXAMPLE 6 G

The synthesis of Example 6 E is repeated, but this time also substituting Aib for Ser$^{33}$, to produce the following peptide: (cyclo 31-34)[Ac-Pro$^4$, D-Phe$^{12}$, Nle$^{21,38}$, CML$^{27,40}$, Glu$^{31}$, Aib$^{33}$, Lys$^{34}$]-r/hCRF(4-41), having the amino acid sequence:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Aib-Lys-Arg-Lys- Leu-Nle-Glu-CML-Ile-NH$_2$, and also its linear counterpart.

Purity of about 98% for the peptides is confirmed by HPLC and by capillary zone electrophoresis (CZE) and identity is confirmed by mass spectroscopy (MS). The measured value of 4496.20 obtained using liquid secondary ion mass spectrometry (LSIMS) for the cyclic peptide is in agreement with the calculated value of 4496.58. The linear peptide has a measured value of 4514.45 which corresponds to the calculated value of 4514.59.

Binding assays with cells expressing human CRFR1 are carried out as described with respect to Example 1. The cloned hCRFR1 binds the cyclic peptide with high affinity as determined by the competitive displacement of bound radioligand. The linear peptide exhibits a slightly higher K$_i$. The difference is significant for similar stably transfected CHO cells expressing human CRFR2 where the respective results for the cyclic and linear peptides show both bind only weakly. The cyclic peptide stimulates the secretion of ACTH and β-END-LI and causes a very significant lowering of blood pressure when administered peripherally

EXAMPLE 6 H

The synthesis of Example 6 E is repeated, but this time also substituting D-Ser for Ser$^{33}$, to produce the following peptide: (cyclo 31-34)[Ac-Pro$^4$, D-Phe$^{12}$, Nle$^{21,38}$, CML$^{27,40}$, Glu$^{31}$, D-Ser$^{33}$, Lys$^{34}$]-r/hCRF(4-41), having the amino acid sequence:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-D-Ser-Lys-Arg-Lys- Leu-Nle-Glu-CML-Ile-NH$_2$, and also its linear counterpart.

Purity of about 96% for the peptides is confirmed by HPLC and by capillary zone electrophoresis (CZE) and identity is confirmed by mass spectroscopy (MS). The measured value of 4498.46 obtained using liquid secondary ion mass spectrometry (LSIMS) for the cyclic peptide is in agreement with the calculated value of 4498.56. The linear peptide has a measured value of 4516.27 which corresponds to the calculated value of 4516.57.

Binding assays with cells expressing human CRFR1 are carried out as described with respect to Example 1. The linear peptide exhibits a slightly higher $K_i$. The difference is significant for similar stably transfected CHO cells expressing human CRFR2 where the respective results for the cyclic and linear peptides show both bind only weakly. The cyclic peptide stimulates the secretion of ACTH and β-END-LI and causes a very significant lowering of blood pressure when administered peripherally.

EXAMPLE 6 I

The synthesis of Example 6 E is repeated, but this time also substituting D-Ala for $Ser^{33}$, to produce the following peptide: (cyclo 31-34)[Ac-$Pro^4$, D-$Phe^{12}$, $Nle^{21,38}$, $CML^{27,40}$, $Glu^{31}$, D-$Ala^{33}$, $Lys^{34}$]-r/hCRF(4-41), having the amino acid sequence:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-D-Ala-Lys-Arg-Lys- Leu-Nle-Glu-CML-Ile-$NH_2$, and also its linear counterpart.

Purity of about 97% for the peptides is confirmed by HPLC and by capillary zone electrophoresis (CZE) and identity is confirmed by mass spectroscopy (MS). The measured value of 4482.47 obtained using liquid secondary ion mass spectrometry (LSIMS) for the cyclic peptide is in agreement with the calculated value of 4482.57. The linear peptide has a measured value of 4500.61 which corresponds to the calculated value of 4500.58.

Binding assays with cells expressing human CRFR1 are carried out as described with respect to Example 1. The cloned hCRFR1 binds the cyclic peptide with high affinity as determined by the competitive displacement of bound radioligand. The linear peptide exhibits a slightly higher $K_i$. The difference is significant for similar stably transfected CHO cells expressing human CRFR2 where the respective results for the cyclic and linear peptides show both bind only weakly. The cyclic peptide stimulates the secretion of ACTH and β-END-LI and causes a very significant lowering of blood pressure when administered peripherally.

CRF profoundly stimulates the pituitary-adrenalcortical axis, and acts within the brain to mediate a wide range of stress responses. These CRF agonists should be useful to stimulate the functions of this axis in some types of patients with low endogenous glucocorticoid production; for example, they should be useful in restoring pituitary-adrenal function in patients having received exogenous glucocorticoid therapy whose pituitary-adrenalcortical functions remain suppressed.

Improving Learning and Memory

As noted above, the present invention provides methods for improving learning and memory through the administration to a patient of a therapeutically effective amount of a CRFR1 ligand. Such patients may be identified through a clinical diagnosis based on symptoms of dementia or learning and memory loss. Individuals with an amnesic disorder are impaired in their ability to learn new information or are unable to recall previously learned information or past events. The memory deficit is most apparent on tasks to require spontaneous recall and may also be evident when the examiner provides stimuli for the person to recall at a later time. The memory disturbance must be sufficiently severe to cause marked impairment in social or occupational functioning and must represent a significant decline from a previous level of functioning. The memory deficit may be age-related or the result of disease or other cause.

Dementia is characterized by multiple clinically significant deficits in cognition that represent a significant change from a previous level of functioning. Memory impairment involving inability to learn new material or forgetting of previously learned material is required to make the diagnosis of a dementia. Memory can be formally tested by asking the person to register, retain, recall and recognize information. The diagnosis of dementia also requires at least one of the following cognitive disturbances: aphasia, apraxia, agnosia or a disturbance in executive functioning. These deficits in language, motor performance, object recognition and abstract thinking, respectively, must be sufficiently severe in conjunction with the memory deficit to cause impairment in occupational or social functioning and must represent a decline from a previously higher level of functioning.

In addition, a number of biochemical tests that correlate levels of CRF with impaired learning and memory may be utilized. For instance, the level of free CRF in the cerebrospinal fluid may be measured by ELISA or RIA. Additionally, or in place of the assays, brain imaging as described with a labeled ligand specific to the CRF-BP or CRF receptor may be used to quantitate free receptor or CRF-BP, thus allowing one to know that free CRF is decreased. Finally, imaging of the brain with a ligand specific to unbound CRF may be used to directly assay the amount of free CRF in the brain.

The patient's minimental status is recorded by the Minimental Test for Learning and Memory, a standard test used by clinicians to determine if a patient has impaired learning and memory (Folstein et al., J. Psychiatric Res. 12:185, 1975). This test involves a number of simple tasks and written questions. For instance, "paired-associate" learning ability is impaired in amnesiac patients of several types including those suffering from head trauma, Korsakoffs disease or stroke (Squire, 1987). Ten pairs of unrelated words (e.g., army-table) are read to the subject. Subjects are then asked to recall the second word when given the first word of each pair. The measure of memory impairment is a reduced number of paired-associate words recalled relative to a matched control group. This serves as an index of short-term, working memory of the kind that deteriorates rapidly in the early stages of dementing or amnesiac disorders.

Improvement in learning and memory constitutes either (a) a statistically significant difference between the performance of ligand-inhibitor treated patients as compared to members of a placebo group; or (b) a statistically significant change in performance in the direction of normality on measures pertinent to the disease model. This strategy has been successfully employed in identifying therapeutically useful cholinomimetics for memory improvement. Animal models or clinical instances of disease exhibit symptoms which are by definition distinguishable from normal controls. Thus, the measure of effective pharmacotherapy will be a significant, but not necessarily complete, reversal of symptoms. Improvement can be facilitated in both animal and human models of memory pathology by clinically effective "cognitive enhancing" drugs which serve to improve performance of a memory task. For example, cognitive enhancers which function as cholinomimetic replacement therapies in patients suffering from dementia and memory loss of the Alzheimer's type significantly improve short-term working memory in such paradigms as the paired-associate task (Davidson and Stem, 1991). Another potential application for therapeutic interventions against memory impairment is suggested by age-related deficits in performance which are effectively modeled by the longitudinal study of recent memory in aging mice (Forster and Lal, 1992).

In animals, several established models of learning and memory are available to examine the beneficial cognitive enhancing effects and potential anxiety-related side effects of activation of CRF-sensitive neurons. The cognitive enhancing effects are measured by the Morris maze (Stewart and Morris, in Behavioral Neuroscience, R. Saghal, Ed. (IRL Press, 1993) p. 107) the Y-maze (Brits et al., Brain Res. Bull. 6, 71 (1981)), one-way active avoidance test, and two-way passive avoidance test; anxiety-related effects are evaluated in the elevated plus-maze. (Pellow et al., J. Neurosci. Meth. 14:149,1985.)

The Morris water maze is one of the best validated models of learning and memory, and it is sensitive to the cognitive enhancing effects of a variety of pharmacological agents (McNamara and Skelton, Brain Res. Rev. 18:33, 1993). The task performed in the maze is particularly sensitive to manipulations of the hippocampus in the brain, an area of the brain important for spatial learning in animals and memory consolidation in humans. Moreover, improvement in Morris water maze performance is predictive of clinical efficacy of a compound as a cognitive enhancer. For example, treatment with cholinesterase inhibitors or selective muscarinic cholinergic agonists reverse learning deficits in the Morris maze animal model of learning and memory, as well as in clinical populations with dementia (McNamara and Skelton, 1993; Davidson and Stem, 1991; McEntee and Crook, 1992; Dawson et al., 1992). In addition, this animal paradigm accurately models the increasing degree of impairment with advancing age (Levy et al., 1994) and the increased vulnerability of the memory trace to pre-test delay or interference (Stewart and Morris, 1993) which is characteristic of amnesiac patients.

The test is a simple spatial learning task in which the animal is placed in tepid water, which is opaque due to the addition of powdered milk. The animals learn the location of the platform relative to visual cues located within the maze and the testing room; this learning is referred to as place learning.

As discussed in more detail below, 15 minutes prior to training on each of days 1-3, groups of animals orally receive control solution or a dosage of the ligand inhibitor. Control animals typically reach the platform within five to ten seconds after three days of training. The measure of the memory modulator effects of a ligand inhibitor is a shift of this time period. Administration of a ligand inhibitor results in a dose-dependent increase in availability of synaptic CRF and a behavioral dose-dependent increase in acquisition and memory retention.

The Y-maze test based on visual discrimination is another assay of learning and memory in animals. In this maze, two arms of the maze end in a translucent plastic panel behind which there is a 40-watt electric bulb. The start box is separated from the third arm by a manually-activated guillotine door. In the first trial, all animals are allowed to explore the maze for 5 minutes, and food pellets are available in each arm. On the second day, each animal is placed in the start box with the door closed. When the door is opened, the animal is allowed to move down the arms and eat the pellets which are located in both arms. On the third day, animals receive six trials in groups of three where one arm is closed at the choice point, no discriminative stimulus is present, and two food pellets are available in the open goal box. On days 4-10, a light at the end of the arm with the food pellets is illuminated and ten trials are run, again in groups of three. The time it takes for the animal to reach the food pellets is recorded.

The effectiveness of a ligand inhibitor to improve learning and memory in the Y-maze is tested as follows. Fifteen minutes prior to each of the blocks of training trials on days 4-10, groups of animals orally receive control solutions or doses of a ligand inhibitor. Control animals are expected to make 50% correct choices. The measure of efficacy of treatment on memory is an increase in correct responses.

The one-way active avoidance test is another assay of learning and memory in animals. It may be used to assess improvement in age-related memory deficits. An animal is placed in a footshock compartment; an opening door to a safe compartment serves as a signal for avoidance. Briefly, in this test an animal is placed in a Skinner box enclosure that contains a grid floor composed of stainless steel bars. A seven watt light and tone generator at each end of the box serve as conditioned stimuli. A rat or mouse is initially trained by being placed in the footshock compartment facing away from the door. A shock is administered simultaneously with the door opening to the safe compartment. At intervals, the test is repeated, only the shock is delayed for 10 seconds after the door is opened. The time it takes the animal to leave the footshock compartment is recorded.

The effectiveness of a ligand inhibitor to improve memory and learning in the one-way avoidance or control solution is tested as follows. Animals are given the ligand inhibitor 15 minutes prior to training. Twenty-four hrs later, the groups are tested for retention, without further administration of ligand inhibitor. The measure of efficacy is a shortened latency time to leaving the footshock compartment.

The two-way passive avoidance test is another assay of learning and memory. An animal is placed in the safe compartment of the Skinner box and when it enters the footshock compartment, the door is closed and a mild shock is administered. The latency time for entering the second compartment is recorded. Memory is tested 1 to 7 days later. At this time, a shock is not administered.

The effectiveness of a ligand inhibitor to improve learning and memory is tested as follows. Immediately prior to training, groups of animals orally receive control solutions or doses of ligand inhibitor. Latency time for entering the footshock compartment is then determined.

The elevated plus maze test measures anxiogenic responses in an approach-avoidance situation involving an exposed, lighted space versus a dark, enclosed space. Both spaces are elevated and are set up as two runways intersecting in the form of a plus sign. This type of approach-avoidance situation is a classical test of "emotionality" and is very sensitive to treatments that produce disinhibition and stress. Animals are placed in the center of the maze and are allowed free access to all four arms in a five minute testing period. The time spent in each arm is recorded.

In humans, methods for improving learning and memory may be measured by such tests as the Wechsler Memory Scale or a pair-associate memory task. The Wechsler Memory Scale is a widely-used pencil-and-paper test of cognitive function and memory capacity. In the normal population, the standardized test yields a mean of 100 and a standard deviation of 15, so that a mild amnesia can be detected with a 10-15 point reduction in the score, a more severe amnesia with a 20-30 point reduction, and so forth (Squire, 1987). During the clinical interview, a battery of tests, including, but not limited to, the Minimental test, the Wechsler memory scale, or paired-associate learning are applied to diagnose symptomatic memory loss. These tests provide general sensitivity to both general cognitive impairment and specific loss of learning/ memory capacity (Squire, 1987). Apart from the specific diagnosis of dementia or amnestic disorders, these clinical instruments also identify age-related cognitive decline which reflects an objective diminution in mental function consequent to the aging process that is within normal limits given the person's age (DSM IV, 1994). As noted above, "improvement" in learning and memory is present within the context of the present invention if there is a statistically significant difference in the direction of normality in the paired-associate test, for example, between the performance of ligand-inhibitor treated patients as compared to members of the placebo group or between subsequent tests given to the same patient.

Decreasing Food Intake

As noted above, the present invention provides methods for decreasing food intake through the administration to a patient of a therapeutically effective amount of a CRFR1 ligand. CRF has been shown to be an important modulator of food intake. For example, administration of CRF agonists or conditions that elevate endogenous CRF levels (e.g., stress) diminish food intake (Appel et al., Endoc. 128:3237, 1991; Krahn and Gosnell, Psychiat. Med. 7:235, 1989; McCarthy et al., Am. J. Physiol. 264:E638, 1993). Thus, administration of CRF causes significant decrease on nocturnal food intake (Gosnell et al., Peptides 4:807, 1983), lowered body weight in rats (Hotta et al., Life Sci. 48:1483, 1991) and increased temperature response in brown adipose tissue (LeFeuvre et al., Neuropharmacol. 26:1217, 1987). Furthermore, neuropeptide Y (NPY), which is the strongest known stimulus of food intake, can be potentiated in its effect upon co-administration of a ligand of the CRF receptor.

Patients may be identified by being obese. An obese individual weighs more than a target weight considered normal for that person's age, gender and height and can be identified objectively by a body mass index (BMI-calculated as weight in kilograms/height in meters$^2$) at or higher than the 85th percentile of the same reference population (National Center for Health Statistics, "Obese and Overweight Adults in the United States." Series 11, No. B0, U.S. Government Printing Office, Washington, D.C., 1983). In addition, evidence that CRF is involved for a particular individual may be obtained by demonstrating decreased CRF levels in the cerebrospinal fluid or by brain imaging as described above. Because the hypothalamus is a common brain area mediating the effects of CRF on food intake and endocrine parameters, alterations in pituitary hormone concentration may also reflect altered levels in hypothalamic CRF.

A decrease in food intake may be measured both in the delayed initiation of a meal and the reduction in the overall duration or quantity of food consumption. Smith, "Satiety and the Problem of Motivation," in D. W. Pfaff (ed.), The Physiological Mechanisms of Motivation, Springer-Verlag, New York, pp. 133-143, 1982. In addition, the selection of particular nutrients in a food choice situation serves as a supplemental measure of specific hunger (Rozin, Adv. Study Behav. 6:21, 1976).

There are two established animal models of appetite regulation. One is a simple measurement of food intake, and the second is a measurement of diet self-selection in a cafeteria environment. In the first method, food intake is limited for 24 hours followed by two hours of access to a preweighed portion of laboratory chow in the animal's home cage. Food intake is measured at 60 and 120 minutes by weighing the remaining pellets. These tests may also be performed on animals that are obese due to genetic mutations and which effectively reproduce symptoms of overeating and deranged nutrient selection (Argiles, Prog. Lipid Res. 28:53, 1989; Wilding et al., Endocrinol. 132:1939, 1993).

In the cafeteria environment, diets are specially formulated with differing proportions of macronutrients, such as carbohydrate, protein, and fat, so as to measure preference for specific nutrients based on sensory attractiveness or post-ingestive benefit. Diet selection is altered, in part, by a wide variety of neurochemical systems. These tests are useful for detection of subtle changes in food intake regulation which impact phenomena, such as craving or binging, and are relevant for the diagnosis of eating disorders, such as anorexia nervosa and obesity. Following establishment of a baseline for animals, 15 minutes prior to testing each animal receives an oral dose of a ligand inhibitor. Food intake is measured as described for the feeding test or the diet self-selection in the cafeteria environment, and test results are compared to baseline. In addition, overeating in an animal model of nicotine withdrawal and in genetically obese rats (Zucker strain) provide other models to test the effect of a ligand inhibitor on appetite regulation. Briefly, in the nicotine withdrawal model, animals are administered nicotine in a chronic fashion. These animals show inhibition of normal weight gain and reduction of food and water intake. Upon cessation of nicotine treatment, animals significantly increase both body weight and intake of food and water. The effect of ligand inhibitors on appetite during nicotine withdrawal is assessed by administering the ligand inhibitor three days following nicotine cessation.

A genetic basis for overeating has been discovered in both mice (e.g., ob/ob) and rats (Zucker strain; fa/fa). These animals offer other models of overeating to assess the efficacy of ligand inhibitors. In particular, Zucker rats are used as subjects. Groups of rats are treated with vehicle or ligand inhibitor on a daily basis over a set time period, such as one week. Subsequent weight gain or food intake is measured. Normal Zucker rats (not genetically obese) serve as controls. Administration of a ligand inhibitor reduces food intake and body weight gain relative to that of normal rats.

In humans, obesity is related not only to overeating, but may also be related to consumption of nutritionally imbalanced diets such as a disproportionately large intake of sweet or fatty foods. (Drewnowski et al., Am. J. Clin. Nutr. 46:442, 1987.) Thus, clinical manifestations of appetite regulation are readily detected using controlled experimental diets or cafeteria self-selection protocols which record intake patterns in terms of quantity, meal duration, and choice (Kissileff, Neurosci. Biobehav. Rev. 8:129, 1984). In these tests, following a baseline determination for each individual, measurement of food intake or self-selection in the cafeteria environment are measured. Improvement in the context of the treatment of obesity constitutes a weight loss or reduction in food intake exhibited by treated patients as compared to members of a placebo group. Moreover, this strategy has been successful in identifying serotonergic agonists for obesity.

Diseases Associated with Low Levels of CRF

As noted above, the present invention provides methods for treating diseases associated with low levels of CRF through the administration to a patient of a therapeutically effective amount of a ligand inhibitor of a CRF/CRF-BP complex. Such patients may be identified through diagnosis of eating disorders, neuroendocrine disorders, and cognitive disorders, such as Alzheimer's disease. In addition, other conditions associated with decreased CRF levels, such as atypical depression, seasonal depression, chronic fatigue syndrome, obesity, vulnerability to inflammation disease, post-traumatic stress disorder, and psychostimulant withdrawal often present a profile of hypothyroidism and decreased stress system activity which is identified characteristically by a decrease in urinary free cortisol and plasma ACTH. Thus, these diseases and conditions would likely be resolved in part by restoration or potentiation of brain CRF levels (Chrousos and Gold, JAMA 267:1244, 1992).

The hallmark of this diverse set of human disease states is dysregulation of the pituitary-adrenal axis with a presumed derangement of brain CRF. Hence, the fact that experimental alternation of CRF/pituitary-adrenal systems in laboratory animals reproduces essential features of the above syndromes, namely behavioral despair (Pepin et al., 1992), exercise fatigue (Rivest and Richard, 1990), obesity (Rothwell, 1989) and hyperarousal associated with psychostimulant withdrawal (Koob et al., 1993; Swerdlow et al., 1991) suggests the broad utility of pharmacotherapies designed to normalize endogenous levels of CRF.

The essential feature of seasonal depression (major depressive disorder with seasonal pattern) is the onset and remission of major depressive episodes at characteristic times of the year. In most cases, the episodes begin in fall or winter and remit in spring. Major depressive episodes that occur in a seasonal pattern are often characterized by prominent anergy, hypersomnia, overeating, weight gain, and a craving for carbohydrates and must persist for a period of at least two weeks during which there is either depressed mood or the loss of interest or pleasure in nearly all activities.

The essential feature of post-traumatic stress disorder is the development of characteristic symptoms following exposure to an extreme traumatic stressor involving direct personal experience of an event that involves actual or threatened death or serious injury to one's own or another's physical integrity. The person's response to the event must involve intense fear, helplessness, or horror. The traumatic event is reexperienced as intrusive recollections or nightmares which trigger intense psychological distress or physiological reactivity. The full symptom picture must be present for more than one month and cause clinically significant distress or impairment in social or occupational functioning.

The essential feature of nicotine withdrawal (nicotine-induced disorder) is the presence of a characteristic withdrawal syndrome that develops after the abrupt cessation of, or reduction in, the use of nicotine-containing products following a prolonged period (at least several weeks) of daily use. Diagnosis of nicotine withdrawal requires identification of four or more of the following: dysphoric or depressed mood, insomnia, irritability or anger, anxiety, difficulty concentrating, restlessness or impatience, decreased heart rate and increased appetite or weight gain. These symptoms must cause clinically significant distress or impairment in social, occupational functioning.

Improvement constitutes either (a) a statistically significant change in the symptomatic condition of a treated individual as compared to a baseline or pretreatment condition on measures pertinent to the disease model; or (b) a statistically significant difference in the symptomatic condition of ligand-inhibitor treated patients and members of a placebo group. Clinical instances of disease exhibit symptoms which are, by definition, distinguishable from normal controls. For depression, several rating scales of depression are used. (See Klerman et al., Clinical Evaluation of Psychotropic Drugs: Principles and Guidelines, Prien and Robinson (eds.), Raven Press, Ltd., New York, 1994). One test, the Hamilton Rating Scale for Depression, is widely used to evaluate depression and is also used to assess symptom changes in response to treatment. Other tests and ratings can be found in the DSM-IV manual. For nicotine withdrawal, as well as the other disorders, tests for evaluation of the severity of the disorder can be found in the DSM-IV manual.

Alzheimer's Disease

As noted above, the present invention provides methods for treating Alzheimer's disease ("AD") through the administration to a patient of a therapeutically effective amount of a CRFR1 ligand. Such patients may be identified through clinical diagnosis based on symptoms of dementia or learning and memory loss which are not attributable to other causes. In addition, patients are also identified through diagnosis of brain atrophy as determined by magnetic resonance imaging.

Decreased levels of CRF are shown to be implicated in Alzheimer's disease. Brains obtained post-mortem from ten individuals with AD and ten neurologically normal controls were chosen for study. Standard areas of frontal pole, parietal pole, temporal pole, and occipital pole were dissected from fresh brain, frozen in dry ice, and stored at −70° C. until they were processed for CRF radioimmunoassay and CRF-BP assay. Formalin-fixed samples of the cerebral cortex and hippocampus were embedded in paraffin and subsequently sectioned and stained with hematoxylin/eosin and silver impregnation. Examination of stained sections from brains of AD patients showed abundant neuritic plaques and neurofibrillary tangles typical of AD, whereas control cases showed none.

Several established animal models of Alzheimer's disease which focus on cholinergic deficits are available. The primary role of cholinergic deficits in AD is well established. In AD, there are significant positive correlations between reduced choline acetyltransferase activity and reduced CRF levels in the frontal, occipital, and temporal lobes (DeSouza et al., 1986). Similarly, there are negative correlations between decreased choline acetyltransferase activity and an increased number of CRF receptors in these three cortices (Id.). In two other neurodegenerative diseases, there are highly significant correlations between CRF and choline acetyltransferase activity in Parkinson's disease, but only a slight correlation in progressive supranuclear palsy (Whitehouse et al., 1987).

In rats, anatomic and behavioral studies evidence interactions between CRF and cholinergic systems. First, in some brain stem nuclei, CRF and acetylcholinesterase are co-localized, and some cholinergic neurons also contain CRF. Second, CRF inhibits carbachol-induced behaviors (carbachol is a muscarinic cholinergic receptor antagonist), suggesting that CRF has effects on cholinergic systems (Crawley et al., Peptides 6:891, 1985). Treatment with another muscarinic cholinergic receptor antagonist, atropine, results in an increase in CRF receptors (DeSouza and Battaglia, Brain Res. 397:401, 1986). Taken together, these data show that CRF and cholinergic systems interact similarly in humans and animals.

An animal model of Alzheimer's disease which focuses on cholinergic deficits is produced by the administration of scopolamine, a non-selective postsynaptic muscarinic receptor antagonist that blocks the stimulation of postsynaptic receptors by acetylcholine. In these animals, memory deficits are readily apparent as measured by passive avoidance or delayed-matching-to-position tests, which distinguish motor or perceptual deficits from amnesia or cognitive enhancing effects of experimental treatments. Thus, the Morris maze and Y-maze tests following scopolamine-induced amnesia are utilized to test memory impairment and subsequent enhancement following administration of ligand inhibitor. In the Morris maze, the design of the experiment is essentially as described above, but is modified to include treatment 30 minutes prior to training on each of days 1 to 3 with an ip injection of scopolamine hydrobromide (0.3 mg/kg). This amnestic dose of scopolamine impairs acquisition and retention of spatial and avoidance learning paradigms in the rat. The anti-amnestic effects of a ligand inhibitor are measured relative to the concurrent control groups who receive or do not receive scopolamine. The effect of the ligand inhibitors on reversal of scopolamine-induced amnesia using the Y-maze is performed similarly to the Y-maze test described above. Modification of this test includes treatment 30 minutes prior to training on days 5 to 10 with an ip injection of scopolamine hydrobromide (0.3 mg/kg). The anti-amnestic effects of a ligand inhibitor administered centrally or systemically are measured relative to concurrent control and scopolamine treated-control groups.

Several tests measuring cognitive behavior in AD have been designed. (See Gershon et al., Clinical Evaluation of Psychotropic Drugs: Principles and Guidelines, Prien and Robinson (eds.), Raven Press, Ltd., New York, 1994, p. 467.) One of these tests, BCRS, measures concentration, recent memory, past memory, orientation, and functioning and self-care. The BCRS is designed to measure only cognitive functions. This test, as well as the Weschler Memory Scale and the Alzheimer's Disease-Associated Scale, may be used to determine improvement following therapeutic treatment with ligand inhibition. As noted above, "improvement" in Alzheimer's disease is present within the context of the present invention if there is a statistically significant difference in the direction of normality in the Weschler Memory Scale test, for example, between the performance of ligand-inhibitor treated patients as compared to members of the placebo group or between subsequent tests given to the same patient. In addition, scopolamine-induced amnesia in humans can be used as a model system to test the efficacy of the ligand inhibitors.

The CRFR1 ligand peptides of the invention will also be therapeutically useful to modulate blood flow in many various vascular beds, and particularly in desired tissues and organs. They should be of use for increasing blood flow to the gastrointestinal tract of animals, particularly humans and other mammals, as they are expected to dilate the mesenteric vascular bed. CRF has been shown to modulate vascular permeability (Wei E. T. et al., "Peripheral anti-inflammatory actions of corticotropin-releasing factor", pp. 258-276, *Corticotropin-Releasing Factor* (Ciba Foundation Symposium 172) John Wiley & Sons, 1993), and these CRFR1 ligands will also reduce vascular leakage and have a salutary effect on injury- or surgery-induced tissue swelling and inflammation. Therefore, these CRFR1 ligands can be administered parenterally to decrease inflammation, swelling and edema and to reduce fluid loss following heat injury.

oCRF, r/hCRF, urotensin I and sauvagine have been shown to inhibit gastric acid production, and the CRFR1 ligands of the invention are considered to also likely be effective in the treatment of gastric ulcers by reducing gastric acid production and/or inhibiting certain gastrointestinal functions in a mammal.

These CRFR1 ligand peptides may also be used to evaluate hypothalamic pituitary adrenal function in mammals with suspected endocrine or central nervous system pathology by suitable administration followed by monitoring bodily functions. For example, administration may be used as a diagnostic tool to evaluate Cushing's disease and affective disorders, such as depressive illness.

CRFR1 ligands or the nontoxic addition salts thereof would normally be administered to mammals, including humans combined with a pharmaceutically or veterinarily acceptable carrier. As used herein, the terms "pharmaceutically acceptable", "physiologically tolerable" and grammatical variations thereof, as they refer to compositions, carriers, diluents and reagents, are used interchangeably. Preferably, the materials are capable of administration to a mammal without the production of undesirable physiological effects, such as nausea, dizziness, gastric upset and the like. The peptides should be at least about 90% pure and preferably should have a purity of at least about 97%. Administration to a patient would be in a therapeutically effective amount, which is an amount calculated to achieve the desired effect, either increasing the level of free CRF in the brain, improving learning and memory, decreasing food intake, activating CRF neurocircuitry in the brain, treating diseases associated with low levels of CRF in the brain, treating the symptoms associated with Alzheimer's disease, treating obesity, treating atypical depression, treating substance abuse withdrawal, treating post-partum depression, or age-related memory loss. It will be apparent to one skilled in the art that the route of administration may vary with the particular treatment and also with whether a peptide or non-peptide ligand inhibitor is administered. Routes of administration may be either non-invasive or invasive. Non-invasive routes of administration include oral, buccal/sublingual, rectal, nasal, topical (including transdermal and ophthalmic), vaginal, intravesical, and pulmonary. Invasive routes of administration include ICV, intraarterial, intravenous, intradermal, intramuscular, subcutaneous, intraperitoneal, intrathecal and intraocular.

Intracerebroventricular (ICV) injections are performed on animals as follows. Animals are anesthetized with halothane and secured in a KOPF stereotaxic instrument. A guide cannula aimed above the lateral ventricle is implanted and anchored to the skull with two stainless steel screws and dental cement. For injections, a 30 gauge stainless steel cannula attached to 60 cm of PE 10 tubing is inserted through the guide to 1 mm beyond its tip. Two microliters of ligand inhibitor are injected by gravity flow over a one minute period simply by raising the tubing above the head of the animal until flow begins. Procedures for the other routes of administration are well known in the art.

The required dosage will vary with the particular condition being treated, with the severity of the condition and with the duration of desired treatment, and multiple dosages may be used for a single day. For parental administration, solutions in peanut oil, in aqueous propylene glycol, or in sterile aqueous solution may be employed. Such aqueous solutions, which are suitably buffered, are especially suitable for intravenous, intramuscular, subcutaneous (s.c.) and intraperitoneal administration. Sterile aqueous media are readily available, and for s.c. administration, corn oil or a 3-6% mannitol solution may be preferred. Such peptides are often administered in the form of pharmaceutically acceptable nontoxic salts, such as acid addition salts or metal complexes. The salts of trifluoroacetic acid and pamoic acid may be preferred.

The peptides should be administered under the guidance of a physician in single or multiple doses, and pharmaceutical compositions will usually contain the peptide in conjunction with a conventional, pharmaceutically-acceptable carrier. These carriers are well known in the art and typically contain non-toxic salts and buffers. Such carriers may comprise buffers like physiologically-buffered saline, phosphate-buffered saline, carbohydrates such as glucose, mannose, sucrose, mannitol or dextrans, amino acids such as glycine, antioxidants, chelating agents such as EDTA or glutathione, adjuvants and preservatives. Acceptable nontoxic salts include acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The effective dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal per day. For the treatment of certain indications daily dosages up to about 100 mg/kg may be employed. The daily dosage may be given in a single dose or up to three divided doses.

As mentioned hereinbefore, CRF receptors have now been cloned and binding affinity tests and binding assays employing CRF receptors are readily carried out with initially identified or synthesized peptides to determine whether such peptides will likely be effective CRFR1 ligands as described in WO 96/18649. Such receptor assays can be used as screens for potential drugs which interact with CRF and/or CRF receptors.

As used herein all temperatures are ° C. and all ratios are by volume. Percentages of liquid materials are also by volume.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. The disclosures of all previously mentioned U.S. patents are expressly incorporated herein by reference.

The invention claimed is:

1. A 38-residue or 39-residue CRF cyclic peptide, or a nontoxic salt thereof, which binds to CRFR1 with an affinity substantially greater than it binds to CRFR2, which peptide has the following formula:

$Y_1$-Pro-Pro-Ile-Ser-Leu-Asp-Leu-Thr-D-Phe-His-$R_{14}$-$R_{15}$-Arg-$R_{17}$-$R_{18}$-$R_{19}$-

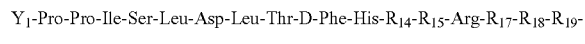
Glu-Nle-Ala-Arg-Ala-Glu-Gln-$R_{27}$-Ala-Gln-Gln-Glu-$R_{32}$-$R_{33}$-Lys-Arg-
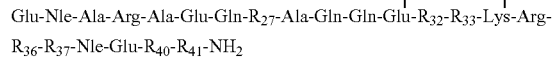
$R_{36}$-$R_{37}$-Nle-Glu-$R_{40}$-$R_{41}$-$NH_2$ wherein the sidechains of Glu and Lys indicated are covalently linked; $Y_1$ is an acyl group having not more than 15 carbon atoms or is radioiodinated tyrosine; $R_{14}$ is CML or Leu; $R_{15}$ is CML or Leu; $R_{17}$ is Glu or CML; $R_{18}$ is Val or CML; $R_{19}$ is CML or Leu; $R_{27}$ is CML or Leu; $R_{32}$ is His or D-His; $R_{33}$ is Aib, D-Ala, D-Ser or Ser; $R_{36}$ is Lys or CML; $R_{37}$ is CML or Leu; $R_{40}$ is Ile or CML; and $R_{41}$ is Ile or CML; provided that D-β-(2-napthyl)alanine(D-2Nal) or D-Leu may be substituted for D-Phe.

2. A CRF agonist peptide, or a nontoxic salt thereof, which binds to CRFR1 with an affinity substantially greater than it binds to CRFR2, which peptide has the following formula:

$Y_1$-Pro-Pro-Ile-Ser-Leu-Asp-Leu-Thr-D-Phe-His-Leu-Leu-Arg-Glu-Val-

Leu-Glu-Nle-Ala-Arg-Ala-Glu-Gln-Leu-Ala-Gln-Gln-Glu-His-Ser-Lys-
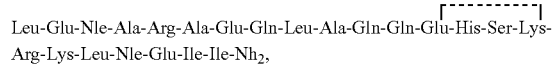
Arg-Lys-Leu-Nle-Glu-Ile-Ile-$Nh_2$, wherein $Y_1$ is an acyl group having not more than 7 carbon atoms or is radioiodinated tyrosine, and wherein a cyclizing bond may exist between the side chains of Glu and Lys as indicated.

3. A 38-residue or 39-residue CRFR1 ligand cyclic peptide which binds to CRFR1 with an affinity substantially greater than it binds to CRFR2, which peptide has the following formula, or a nontoxic salt thereof:

$Y_1$-Pro-Pro-$R_6$-Ser-$R_8$-Asp-Leu-$R_{11}$-D-Phe-His-$R_{14}$-$R_{15}$-Arg-Glu-$R_{18}$-Leu-

$R_{20}$-Nle-$R_{22}$-$R_{23}$-Ala-$R_{25}$-Gln-$R_{27}$-Ala-$R_{29}$-Gln-Glu-$R_{32}$-$R_{33}$-$R_{34}$-Arg-$R_{36}$-
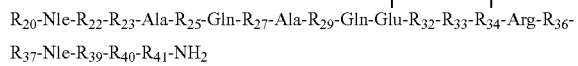
$R_{37}$-Nle-$R_{39}$-$R_{40}$-$R_{41}$-$NH_2$ wherein the side chains of Glu and $R_{34}$ are covalently linked as indicated; $Y_1$ is an acyl group having not more than 7 carbon atoms or is radioiodinated tyrosine; $R_6$ is Ile, Met or Nle; $R_8$ is Leu or Ile; $R_{11}$ is Thr or Ser; $R_{14}$ is CML or Leu; $R_{15}$ is Leu or CML; $R_{18}$ is Val, CML, Nle or Met; $R_{20}$ is Glu or D-Glu; $R_{22}$ is Ala or Thr; $R_{23}$ is Arg or Lys; $R_{25}$ is Asp or Glu; $R_{27}$ is Leu or CML; $R_{29}$ is Gln or Glu; $R_{32}$ is His, Aib, Ala, Gly, Leu, Gln or Glu; $R_{33}$ is Aib or an L- or D-isomer of Ser, Asn, Leu, Ala, CML or Ile; $R_{34}$ is Lys or Orn; $R_{36}$ is Lys or Leu; $R_{37}$ is CML or Leu; $R_{39}$ is Glu or Asp; $R_{40}$ is Ile, CML or Glu; and $R_{41}$ is Ala, Aib or Ile; provided that D-β-(2-napthyl)alanine (D-2Nal) or D-Leu may be substituted for D-Phe.

4. A CRF cyclic peptide according to claim 3 having the formula:

$Y_1$-Pro-Pro-$R_6$-Ser-$R_8$-Asp-Leu-$R_{11}$-D-Phe-His-$R_{14}$-Leu-Arg-Glu-$R_{18}$-Leu-

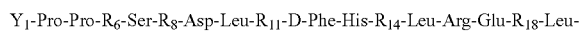
$R_{20}$-Nle-$R_{22}$-$R_{23}$-Ala-$R_{25}$-Gln-Leu-Ala-$R_{29}$-Gln-Glu-$R_{32}$-$R_{33}$-$R_{34}$-Arg-
$R_{36}$-$R_{37}$-Nle-$R_{39}$-$R_{40}$-$R_{41}$-$NH_2$ wherein $Y_1$ is an acyl group having not more than 7 carbon atoms; $R_{20}$ is Glu or D-Glu; $R_{22}$ is Ala or Thr; $R_{23}$ is Arg or Lys; $R_{29}$ is Gln or Glu; $R_{32}$ is His, Aib or Ala; $R_{36}$ is Lys or Leu; $R_{37}$ is Leu or CML; $R_{39}$ is Glu or Asp; $R_{40}$ is Ile, CML or Glu; and $R_{41}$ is Ile, Aib or Ala; wherein the remaining variabies are as defined in claim 3.

5. A peptide according to claim 3 wherein $R_{18}$ is Val, $R_{22}$ is Ala, $R_{23}$ is Arg, $R_{25}$ is Glu, $R_{39}$ is Glu, and $R_{41}$ is Ile.

6. A peptide according to claim 3 having the following formula, or a nontoxic salt thereof:

$Y_1$-Pro-Pro-Ile-Ser-Leu-Asp-Leu-Thr-D-Phe-His-Leu-Leu-Arg-Glu-Val-

Leu-Glu-Nle-$R_{22}$-$R_{23}$-Ala-Glu-Gln-$R_{27}$-Ala-Gln-Gln-Glu-$R_{32}$-$R_{33}$-Lys-
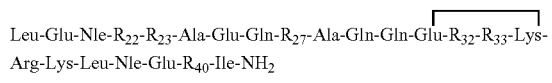
Arg-Lys-Leu-Nle-Glu-$R_{40}$-Ile-$NH_2$ wherein $Y_1$ is an acyl group having not more than 7 carbon atoms; $R_{22}$ is Ala or Thr; $R_{23}$ is Arg or Lys; $R_{27}$ is Leu or CML; $R_{32}$ is His; $R_{33}$ is Ser or Aib; and $R_{40}$ is Ile or CML.

7. A peptide according to claim 1 having the formula:

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Glu-His-Ser-Lys-Arg-Lys-Leu-Nle-Glu-Ile-Ile-Nh$_2$, or

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Ser-Lys-Arg-Lys-Leu-Nle-Glu-Ile-CML-NH$_2$; or

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Aib-Lys-Arg-Lys-Leu-Nle-Glu-Ile-CML-NH$_2$.

8. A peptide according to claim 1 having the formula:

Ac-Pro-Pro-Ile-Ser-Leu-Asp-Leu-Thr-D-Phe-His-Leu-CML-Arg-Glu-Val-Leu-Glu-Nle-Ala-Arg-Ala-Glu-Gln-Leu-Ala-Gln-Gln-Glu-His-Ser-Lys-Arg-Lys-Leu-Nle-Glu-Ile-Ile-NH$_2$, or

Ac-Pro-Pro-Ile-Ser-Leu-Asp-Leu-Thr-D-Phe-His-CML-Leu-Arg-Glu-Val-Leu-Glu-Nle-Ala-Arg-Ala-Glu-Gln-Leu-Ala-Gln-Gln-Glu-His-Ser-Lys-Arg-Lys-Leu-Nle-Glu-Ile-Ile-NH$_2$; or

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Ser-Lys-Arg-Lys-Leu-Nle-Glu-CML-Ile-NH$_2$.

9. A peptide having the formula:

Ac-Pro-Pro-Ile-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Gln-Glu-His-Ser-Lys-Arg-Lys-Leu-Nle-Asp-Ile-Ala-NH$_2$; or

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-CML-Ala-Gln-Gln-Glu-His-Ser-Lys-Arg-Lys-Leu-Nle-Asp-Ile-Ile-NH$_2$; or

Ac-Pro-Pro-Ile-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Gln-Glu-His-Aib-Lys-Arg-Lys-Leu-Nle-Glu-Ile-Ile-NH$_2$.

* * * * *

UNITED STATES PATENT AND TRADEMARK OFFICE
CERTIFICATE OF CORRECTION

PATENT NO. : 7,498,300 B2  Page 1 of 1
APPLICATION NO. : 10/763935
DATED : March 3, 2009
INVENTOR(S) : Jean E. F. Rivier et al.

It is certified that error appears in the above-identified patent and that said Letters Patent is hereby corrected as shown below:

On the Title page, Item (75) Inventors, "Wyle W. Vale, Jr." should read --Wylie W. Vale, Jr.--.

At column 32, line 48-49, "variabies" should read --variables--.

At column 33, line 7, "-Nh$_2$" should read -- -NH$_2$--.

At column 34, line 7, " Glu-His-Ser-Lys " should read -- Glu-His-D-Ser-Lys --.

At column 34, line 17, "-NHo$_2$r" should read -- -NH$_2$--.

At column 34, line 21, "Asp" should be --Glu--.

Signed and Sealed this

Twelfth Day of May, 2009

JOHN DOLL
*Acting Director of the United States Patent and Trademark Office*